United States Patent
Kim et al.

(10) Patent No.: US 10,494,356 B2
(45) Date of Patent: Dec. 3, 2019

(54) COMPOUND PROMOTING OSTEOBLAST DIFFERENTIATION AND INHIBITING ADIPOCYTE DIFFERENTIATION, PREPARATION METHOD THEREOF AND APPLICATION THEREOF

(71) Applicant: SUNG KYUN BIOTECH CO., LTD., Gyeonggi-do (KR)

(72) Inventors: Hyun Suk Kim, Seoul (KR); Kimoon Park, Gyeonggi-do (KR); Min-hyuk Bang, Jeollabuk-do (KR); Hee-Jin Yang, Seoul (KR); Yun Mi Lee, Seoul (KR); Ki Hyun Kim, Gyeongsangnam-do (KR)

(73) Assignee: SUNG KYUN BIOTECH CO., LTD. (KR)

( * ) Notice: Subject to any disclaimer, the term of this patent is extended or adjusted under 35 U.S.C. 154(b) by 0 days.

(21) Appl. No.: 16/300,086

(22) PCT Filed: May 12, 2017

(86) PCT No.: PCT/KR2017/004972
§ 371 (c)(1),
(2) Date: Nov. 9, 2018

(87) PCT Pub. No.: WO2017/209410
PCT Pub. Date: Dec. 7, 2017

(65) Prior Publication Data
US 2019/0152935 A1    May 23, 2019

(30) Foreign Application Priority Data

May 31, 2016 (KR) .................. 10-2016-0067570
May 12, 2017 (KR) .................. 10-2017-0059133

(51) Int. Cl.
*A61K 31/34* (2006.01)
*C07D 307/12* (2006.01)
(Continued)

(52) U.S. Cl.
CPC ............ *C07D 307/12* (2013.01); *A23L 33/10* (2016.08); *A61P 3/14* (2018.01); *A61P 19/08* (2018.01);
(Continued)

(58) Field of Classification Search
CPC ........ C07D 307/12; A23L 33/10; A61P 19/08; A61P 3/14; A23V 2200/306; A23V 2002/00; A23V 2250/02
(Continued)

(56) References Cited

FOREIGN PATENT DOCUMENTS

KR    1020150055667    5/2015

OTHER PUBLICATIONS

Nelson et al., "Postmenopausal Hormone Replacement Therapy", JAMA, vol. 288, No. 7, pp. 872-881, Aug. 21, 2001.
Coleman, "Risks and benefits of bisphosphonates", British Journal of Cancer, 98, pp. 1736-1740 (2008).
Lu et al., "Preparation and relevance of a cross-coupling product between sinapyl alcohol and sinapyl p-hydroxybenzoate", Org. Biomol. Chem., 2, pp. 2888-2890 (2004).
(Continued)

*Primary Examiner* — Taylor V Oh
(74) *Attorney, Agent, or Firm* — Duane Morris LLP; Gregory M. Lefkowitz; Jason M. Nolan

(57) ABSTRACT

The present disclosure relates to a compound having the activity of promoting osteoblast differentiation and inhibiting adipocyte differentiation and a preparation method thereof. The novel compound of the present disclosure increases the expression of the gene ALP involved in the differentiation of osteoblasts, regulates expression of the genes PPARγ, aP2 and CD36 involved in the differentiation of adipocytes, increases bone mineral density (BMD) in an ovariectomized osteoporosis animal model and decreases adipocytes in the bone marrow. Therefore, it can be used as
(Continued)

an active ingredient of a medication or a health functional food useful for metabolic bone disease or obesity.

17 Claims, 15 Drawing Sheets

(51) Int. Cl.
    *A61P 3/14*     (2006.01)
    *A61P 19/08*     (2006.01)
    *A23L 33/10*     (2016.01)

(52) U.S. Cl.
    CPC ..... *A23V 2002/00* (2013.01); *A23V 2200/306* (2013.01); *A23V 2250/02* (2013.01)

(58) Field of Classification Search
    USPC ........................................................ 514/461
    See application file for complete search history.

(56) References Cited

OTHER PUBLICATIONS

Lee et al., "Phenolic Compounds from the Leaves and Twigs of Osteomeles schwerinae That inhibit Rat Lens Aldose Reductase and Vessel Dilation in Zebrafish Larvae", Downloaded by Univ of California Santa Barbara on Sep. 9, 2015, Publication Date Web, 6 pages, Sep. 2, 2015.

Yamauchi et al., Structure-Plant Phytotoxic Activity Relationship of 7.7'-epoxylignanes, (+)- and (-) -verrucosin:L Simplification of the aromatic ring substituents, Biooganic & Medicinal Chemistry Letters, 24, pp. 4798-4803 (2014).

Johnson et al., "Lipophilic stinging nettle extracts possess potent anti-inflammatory activity, are not cytotoxic and may be superior to traditional tinctures for treating inflammatory disorders", Phytomedicine 20, pp. 1430147 (2013).

Lemay, "The relevance of the Women's Health Initiative Results on Combined Hormone Replacement Therapy in Clinical Practice", J. Obstet. Gynaecol. Can., 24(9), pp. 711-715 (2002).

COMPOUND PROMOTING OSTEOBLAST DIFFERENTIATION AND INHIBITING ADIPOCYTE DIFFERENTIATION, PREPARATION METHOD THEREOF AND APPLICATION THEREOF

TECHNICAL FIELD

The present disclosure relates to a novel compound promoting osteoblast differentiation and inhibiting adipocyte differentiation and a preparation method thereof. The novel compound of the present disclosure may be used for preparation of a health functional food or a medication related with metabolic bone disease or obesity.

BACKGROUND ART

The bone is an important part of the body that structurally supports muscles, organs and soft tissues of the human body, surround and protects internal organs from external impact, and stores calcium or other essential minerals such as phosphorus or magnesium in the body.

The bone is composed of osteoblasts, osteocytes, osteoclasts. Among them, the osteoblasts are derived from mesenchymal stem cells which can differentiate into chondrocytes, myocytes and adipocytes and play a role in forming bone tissues through the proliferation, bone matrix formation and calcification stages. And, the osteoclasts are involved in bone resorption.

The old bone of an adult is removed by the osteoclasts and new bone is created by the osteoblasts through the bone remodeling process of repeated bone resorption and creation. For example, the osteoblasts maintain the homeostasis of bone metabolism as they regulate the differentiation of the osteoclasts responsible for bone resorption by secreting RANKL (receptor activator of nuclear factor-κB ligand) and its decoy receptor OPG (osteoprotegerin).

A disruption of the homeostasis of bone metabolism due to a specific cause results in metabolic bone diseases such as osteoporosis, osteodystrophy, fracture, etc.

Osteoporosis, which is a representative metabolic bone disease, refers to a condition of increased risk of fracture due to increased bone weakness where bone mineral density decreases below 2.5 or T-score (standard deviation from the average bone mass of normal adults) decreases below −2.5. Osteoporosis occurs frequently in postmenopausal women. It is known that the bone matrix is decreased with aging and adipocytes occupying the void inhibit the function and differentiation of the bone-creating osteoblasts and promote the function and differentiation of the osteoclasts responsible for bone resorption by secreting inflammatory cytokines. A severe reduction in bone density can easily result in fracture even with a small impact. Although osteoporosis itself has no symptoms, fractures, especially the fracture of the thighbone, vertebral column, etc., caused by bone weakness make it impossible to live a healthy life and, consequently, cause 15% of death in the elderly.

Osteodystrophy is a disease of the bone caused by chronic renal failure, etc. It occurs due to congenitally abnormal kidney function and can lead to death unless dialysis is performed. This bone disease is called renal osteodystrophy. Bone diseases associated with the osteodystrophy include osteomalacia, osteitis fibrosa, etc.

Calcium supplements are recommended for the treatment or prevention of the metabolic bone diseases. For postmenopausal women, vitamin D or hormone drugs such as estrogen or calcitonin are recommended. In addition, bisphosphonate-based bone resorption inhibitors such as Fosamax (alendronate) and Actonel (risedronate), which inhibit osteoclasts and induces their death, are mainly used.

However, it is known that, although the calcium supplements prevent the decrease in bone mass caused by bone resorption by suppressing the secretion of parathyroid hormone, the effect varies greatly among individuals. Also, although the hormone drugs increase bone density, they are reported to have side effects such as breast cancer, myocardial infarction, venous thrombosis, etc. (Nelson, H. D et al., *JAMA*, 288: 872-881, 2002; Lemay, A., *J. Obstet. Bynaecol. Can.*, 24: 711-7152-3). As for the bisphosphonate drugs, the cases of necrosis of the jaw, severe atrial fibrillation, atrophy of bone or joint or pain of the skeletal muscle are reported (Coleman R E., *Br J Cancer*, 98: 1736-1740 (2008).

In addition, although the existing drugs for treating or preventing metabolic bone diseases have the pharmacological activity of preventing further bone loss, they do not provide the effect of restoring decreased bone mass to the original state.

The inventors of the present disclosure have identified that a newly synthesized novel compound can treat and prevent metabolic bone diseases or obesity through regulation of osteoblast and adipocyte differentiation and have completed the present disclosure.

DISCLOSURE

Technical Problem

The present disclosure is directed to providing a composition for preventing or treating metabolic bone disease, which contains a novel compound as an active ingredient.

The present disclosure is also directed to providing a health functional food for improving or preventing metabolic bone disease, which contains a novel compound as an active ingredient.

The present disclosure is also directed to providing a novel compound which has the activity of promoting osteoblast differentiation and inhibiting adipocyte differentiation.

The present disclosure is also directed to providing a method for preparing a novel compound which has the activity of promoting osteoblast differentiation and inhibiting adipocyte differentiation.

Technical Solution

A composition for preventing or treating metabolic bone disease of the present disclosure contains a compound of Chemical Formula 1, an isomer thereof or a pharmaceutically acceptable salt thereof as an active ingredient.

And, a health functional food for improving or preventing metabolic bone disease of the present disclosure contains a compound of Chemical Formula 1, an isomer thereof or a pharmaceutically acceptable salt thereof as an active ingredient.

A compound having the activity of promoting osteoblast differentiation and inhibiting adipocyte differentiation of the present disclosure is a compound of Chemical Formula 1.

[Chemical Formula 1]

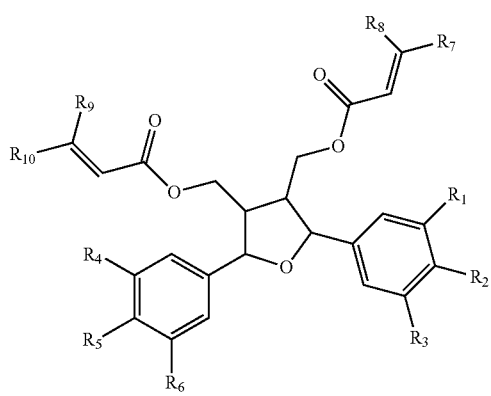

wherein each of $R_1$, $R_2$, $R_3$, $R_4$, $R_5$ and $R_6$, which may be identical or different from each other, is independently selected from a group consisting of hydrogen, hydroxy, $C_1$-$C_6$ alkyl, $C_1$-$C_6$ alkoxy, halogen and trifluoromethyl, and each of $R_7$, $R_8$, $R_9$ and $R_{10}$, which may be identical or different from each other, is independently hydrogen or phenyl, with the proviso that $R_8$ and $R_{10}$ are phenyl if $R_7$ and $R_9$ are hydrogen and $R_8$ and $R_{10}$ are hydrogen if $R_7$ and $R_9$ are phenyl and the phenyl is unsubstituted or substituted with a substituent selected from a group consisting of hydroxy, halogen and trifluoromethyl.

Specifically, each of $R_1$, $R_3$, $R_4$ and $R_6$, which may be identical or different from each other, is independently selected from a group consisting of $C_1$-$C_6$ alkyl and $C_1$-$C_6$ alkoxy, and each of $R_2$ and $R_5$, which may be identical or different from each other, is independently selected from a group consisting of hydrogen, hydroxy, halogen and trifluoromethyl.

More specifically, the compound of Chemical Formula 1 is a compound of Chemical Formula 7, Chemical Formula 8 or Chemical Formula 9.

[Chemical Formula 7]

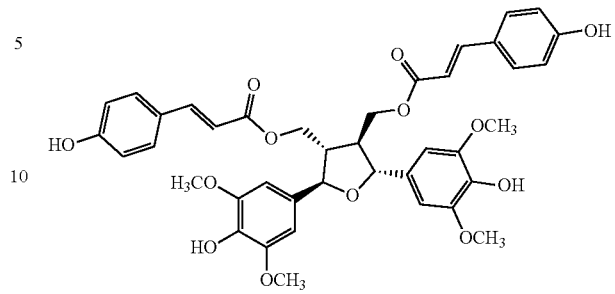

[Chemical Formula 8]

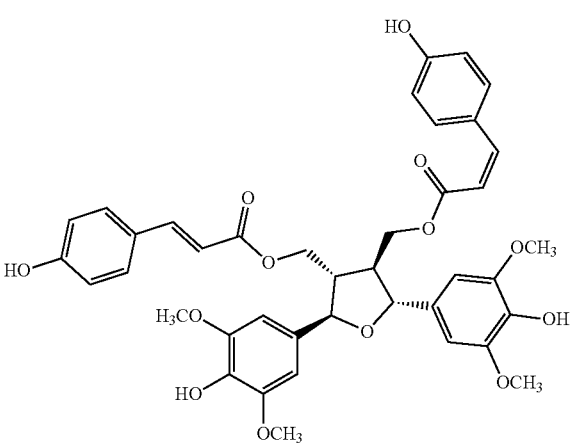

[Chemical Formula 9]

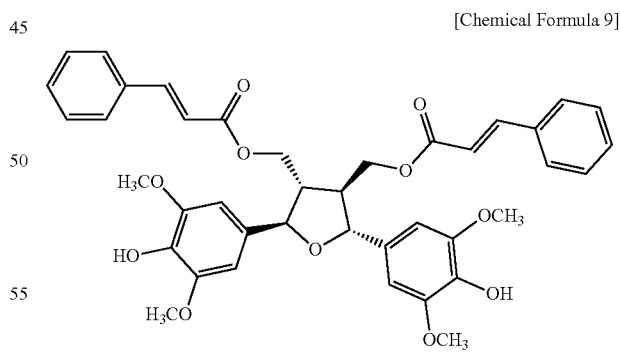

The compound of Chemical Formula 7 having the activity of promoting osteoblast differentiation and inhibiting adipocyte differentiation may be prepared by a preparation method including: a step of preparing a compound of Chemical Formula 6 by reacting a compound of Chemical Formula 4 with a compound of Chemical Formula 5; and a step of removing the MOM protecting group from the compound of Chemical Formula 6.

[Chemical Formula 4]

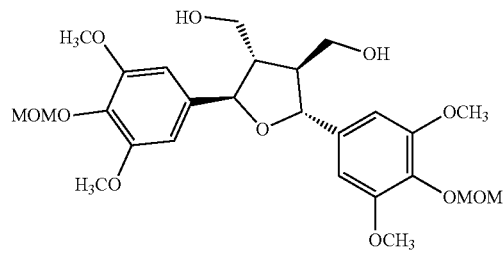

[Chemical Formula 5]

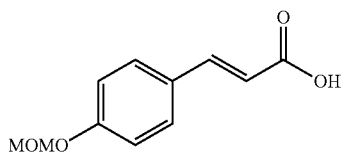

[Chemical Formula 6]

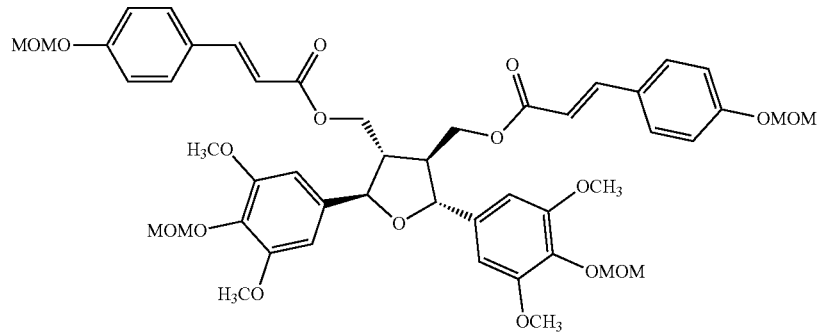

The compound of Chemical Formula 7 having the activity of promoting osteoblast differentiation and inhibiting adipocyte differentiation may be prepared by a preparation method further including: a step of preparing a compound of Chemical Formula 3 by reacting a compound of Chemical Formula 2 with chloromethyl methyl ether; and a step of preparing the compound of Chemical Formula 4 by reacting the compound of Chemical Formula 3 with diisobutylaluminum hydride.

[Chemical Formula 2]

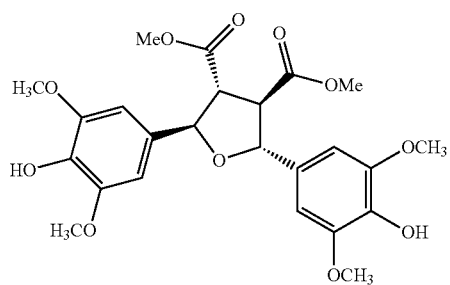

[Chemical Formula 3]

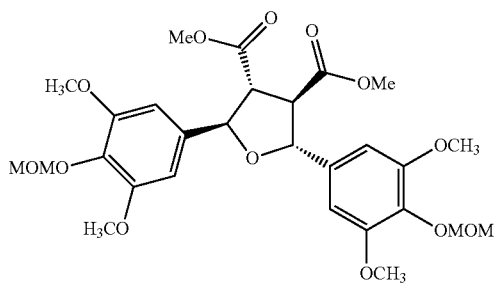

The compound of Chemical Formula 2 may be synthesized from 4-hydroxy-3,5-dimethoxycinnamic acid.

In Chemical Formulas 3-6, 'MOMO-' indicates methoxymethyl, which is one of hydroxyl-protecting groups, ester-bonded to a hydroxyl group. As the hydroxyl-protecting group, a functional group which can be easily removed after completion of a desired chemical reaction and is suitable for protecting the hydroxy group from the chemical reaction is used. In general, such functional groups include unsubstituted or substituted aryl, aralkyl, acyl or alkyl groups. The characteristics and size of the hydroxyl-protecting groups are of no importance because they are removed after the desired chemical reaction or reaction sequence. Specifically, the functional groups may have 1-20, particularly 1-10, carbon atoms. The hydroxy-protecting group may be, for example, benzyl, methoxymethyl, 4-methoxybenzyl, p-nitrobenzoyl, p-toluenesulfonyl, tert-butyl or acetyl, specifically benzyl or methoxymethyl.

The term 'pharmaceutically acceptable salt' used in the present disclosure refers to a salt of a compound which does not cause severe stimulation in an organism to which it is administered without negatively affecting the biological activity and physical properties of the compound. The pharmaceutically acceptable salt includes an acid addition salt formed from an acid which forms a pharmaceutically acceptable nontoxic acid addition salt containing an anion, for example, an inorganic acid such as hydrochloric acid, sulfuric acid, nitric acid, phosphoric acid, hydrobromic acid, hydroiodic acid, etc., an organic carboxylic acid such as tartaric acid, formic acid, citric acid, acetic acid, trichloroacetic acid, trifluoroacetic acid, gluconic acid, benzoic acid, lactic acid, fumaric acid, maleic acid, salicylic acid, etc., a sulfonic acid such as methanesulfonic acid, ethanesulfonic acid, benzenesulfonic acid, p-toluenesulfonic acid, etc., or the like. For example, the pharmaceutically acceptable carboxylic acid salt may include a metal salt or an alkaline earth metal salt formed by lithium, sodium, potassium, calcium, magnesium, etc. an amino acid salt such as lysine, arginine, guanidine, etc., an organic salt such as dicyclohexylamine, N-methyl-D-glucamine, tris(hydroxyethyl)methylamine, diethanolamine, choline, trimethylamine, etc., or the like.

The term 'as an active ingredient' used in the present disclosure means that the compound of Chemical Formula 1 is contained in an amount enough for achieving the desired effect or activity.

The metabolic bone disease includes osteoporosis, osteodystrophy, fracture, etc.

The 'osteoporosis' is diagnosed clinically based on bone density (BMD) and includes all of osteopenia, osteoporosis and severe osteoporosis. In addition, it also includes primary osteoporosis such as type 1 osteoporosis (postmenopausal osteoporosis) and type 2 osteoporosis (senile osteoporosis) and secondary osteoporosis.

The 'osteodystrophy' includes osteomalacia, osteitis fibrosa, etc.

The 'fracture' refers to a condition in which the continuity of a bone or cartilage is lost completely or incompletely or deformed linearly. The fracture may be classified depending on anatomical location, degree of fracture, direction of fracture faces, presence of open wound, number of fragments, stability or displacement of fragments. It may also be classified into pathologic fracture caused by osteoporosis, osteomyelitis, etc. or stress fracture caused by repeated stress.

The composition for preventing or treating metabolic bone disease of the present disclosure has the activity of promoting osteoblast differentiation and inhibiting adipocyte differentiation. Accordingly, it can prevent or treat obesity and metabolic bone disease at the same time.

The composition for preventing or treating metabolic bone disease of the present disclosure may further contain a drug, vitamin, natural product or its extract, which has the activity of preventing or treating metabolic bone disease, together with the compound of Chemical Formula 1. For example, it may contain one or more of a calcium supplement, vitamin D, a hormone drug such as estrogen or calcitonin or a bisphosphonate-based bone resorption inhibitor such as Fosamax (alendronate) or Actonel (risedronate), together with the compound of Chemical Formula 1.

The composition for preventing or treating metabolic bone disease of the present disclosure may contain one or more pharmaceutically acceptable carrier in addition to the above-described active ingredient. As the pharmaceutically acceptable carrier, one or more of saline, sterile water, Ringer's solution, buffered saline, dextrose solution, maltodextrin solution, glycerol and ethanol may be used and, if necessary, other common additives such as an antioxidant, a buffer, a bacteriostat, etc. may be added. Also, the composition may be formulated as an injectable formulation such as an aqueous solution, a suspension, an emulsion, etc., a pill, a capsule, a granule or a tablet by further adding a diluent, a dispersant, a surfactant, a binder or a lubricant. Specifically, it may be formulated according to a method known in the art or the method described in Remington's Pharmaceutical Sciences (Mack Publishing Company, Easton Pa.).

The composition for preventing or treating metabolic bone disease of the present disclosure may be administered orally or parenterally (e.g., intravenously, intraabdominally, subcutaneously or topically) depending on purposes and the administration dosage varies depending on the body weight, age, sex and physical condition of a patient, diet, administration time, administration method, excretion rate, severity of the disease, etc. In the present disclosure, the administration dosage of the compound of Chemical Formula 1 may be 0.1 mg/kg to 10 g/kg, specifically 1 mg/kg to 1 g/kg, per day. The administration may be made once or several times a day.

The health functional food for improving or preventing metabolic bone disease of the present disclosure has the activity of promoting osteoblast differentiation and inhibiting adipocyte differentiation. Accordingly, it can improve or prevent obesity and metabolic bone disease at the same time.

The health functional food for improving or preventing metabolic bone disease of the present disclosure may contain a vitamin, natural product or its extract, which has the activity of improving or preventing metabolic bone disease, together with the compound of Chemical Formula 1. For example, it may contain one or more of a calcium supplement, vitamin D, etc., together with the compound of Chemical Formula 1.

The health functional food for improving or preventing metabolic bone disease of the present disclosure may further contain a sitologically acceptable food additive in addition to the above-described active ingredient.

The health functional food of the present disclosure includes various foods, gum, tea, vitamin complexes, health supplement foods, etc. and may be in the form of a powder, a granule, a tablet, a capsule or a drink.

When the compound of Chemical Formula 1 is added to a food or drink for the purpose of improving or preventing metabolic bone disease, the amount of the compound in the food may be 0.001-5 wt % based on the total food weight and the amount of the compound in the drink may be 0.002-5 g, specifically 0.03-1 g, based on 100 mL of the drink, in general.

The ingredients of the drink are not specially limited except that the compound of Chemical Formula 1 is added as the active ingredient. Various flavorants, natural carbohydrates, etc. may be further contained as in common drinks. Examples of the natural carbohydrate include common sugars such as monosaccharides, e.g., glucose, fructose, etc., disaccharides, e.g., maltose, sucrose, etc. and polysaccharides, e.g., dextrin, cyclodextrin, etc., and sugar alcohols such as xylitol, sorbitol, erythritol, etc. In addition, natural flavorants (thaumatin, stevia extract (e.g., rebaudioside A, glycyrrhizin, etc.) or synthetic flavorants (saccharin, aspartame, etc.) may be used as the flavorant. The content of the natural carbohydrate is usually about 1-20 g, specifically about 5-12 g, per 100 mL of the drink.

In addition, the health functional food of the present disclosure may contain various nutrients, vitamins, minerals (electrolytes), flavors such as synthetic flavors, natural flavors, etc., coloring agents, extenders (cheese, chocolate, etc.), pectic acid and its salts, alginic acid and its salts, organic acids, protective colloidal thickeners, pH modifiers, stabilizers, antiseptics, glycerin, alcohols, carbonating agents used in carbonated drinks, etc. In addition, the health functional food of the present disclosure may contain pulps for preparing natural fruit juices, fruit juice drinks and vegetable drinks. These ingredients may be used either independently or in combination. Although the content of these additives is of no great importance, it is generally selected from a range of about 0.1-20 parts by weight based on 100 parts by weight of the health functional food of the present disclosure.

Advantageous Effects

The present disclosure relates to a compound having the activity of promoting osteoblast differentiation and inhibiting adipocyte differentiation and a preparation method thereof. The novel compound of the present disclosure increases the expression of the gene ALP involved in the differentiation of osteoblasts, regulates expression of the genes PPARγ, aP2 and CD36 involved in the differentiation of adipocytes, increases bone mineral density (BMD) in an ovariectomized osteoporosis animal model and decreases adipocytes in the bone marrow. Therefore, it can be used as an active ingredient of a medication or a health functional food useful for metabolic bone disease or obesity.

MODE FOR CARRYING OUT INVENTION

Figure 1:
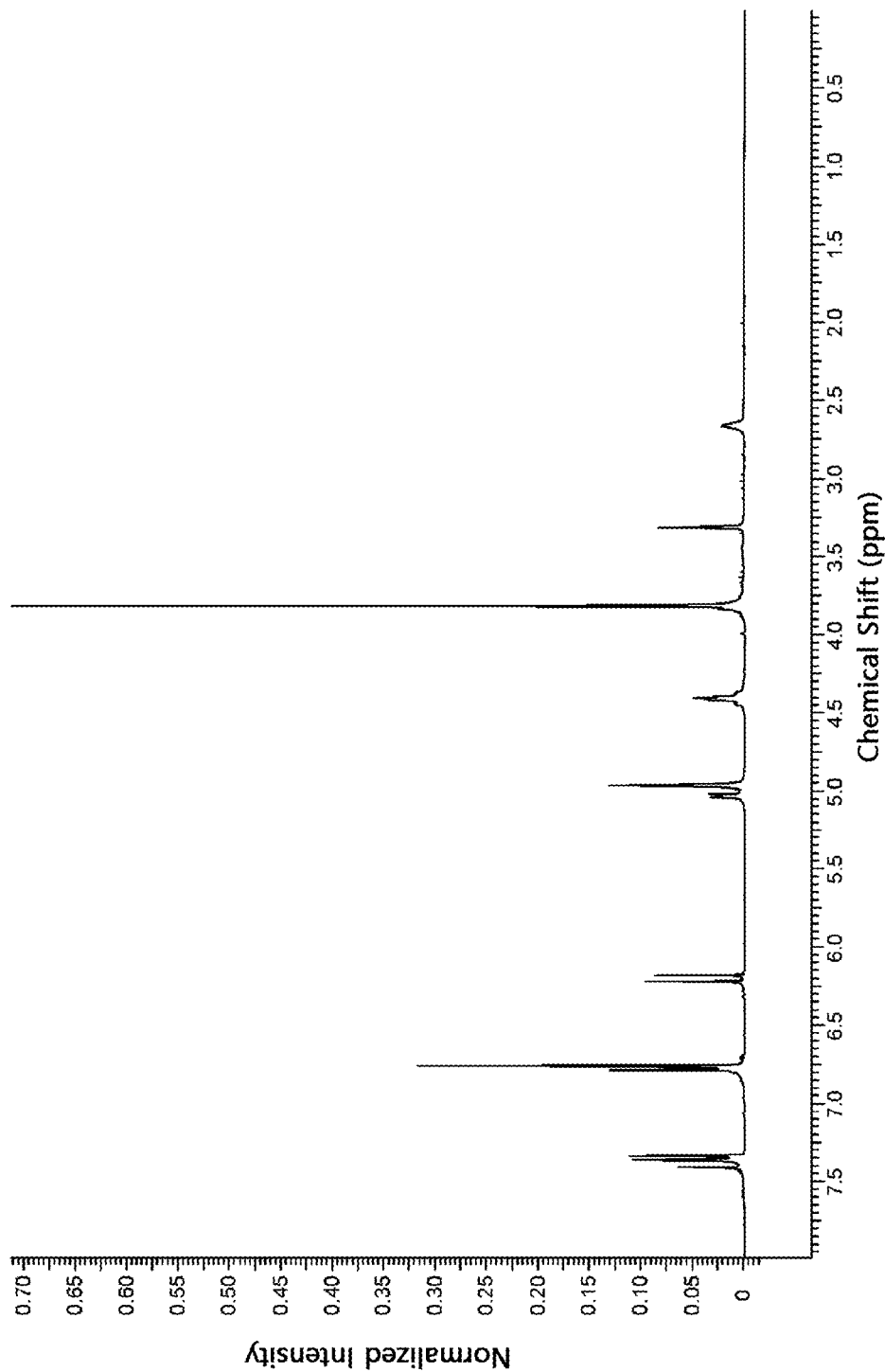
FIG. 1 shows the $^1$H NMR spectrum of the NK11 compound.
Figure 2:
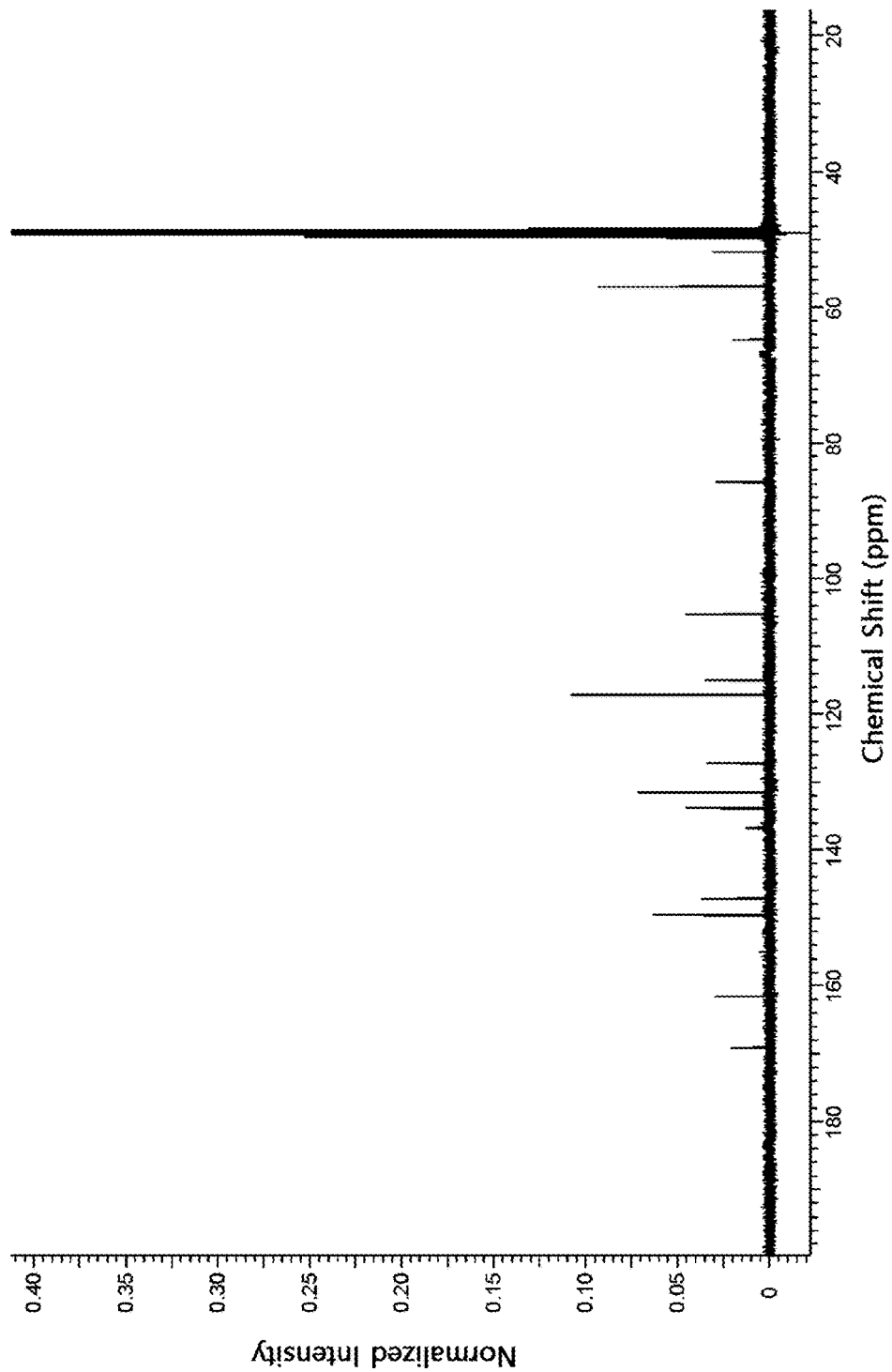
FIG. 2 shows the $^{13}$C NMR spectrum of the NK11 compound.

Hereinafter, the present disclosure will be described in detail through examples and test examples. However, the following examples and test examples are for illustrative purposes only and the present disclosure is not limited by them.

PREPARATION EXAMPLE 1

Synthesis of Compound of Chemical Formula 3 (dimethyl 2,5-bis(3,5-dimethoxy-4-(methoxymethoxy)phenyl)tetrahydrofuran 3,4-dicarboxylate)

The compound of Chemical Formula 2 was prepared from 4-hydroxy-3,5-dimethoxycinnamic acid using the known synthesis method.

After adding the furan compound of Chemical Formula 2 (401 mg, 0.812 mmol) to a 10-mL round-bottom flask, dichloromethane ($CH_2Cl_2$, 3 mL), diisopropylethylamine (495 μL, 2.84 mmol) and chloromethyl methyl ether (216 μL, 2.843 mmol) were added under a nitrogen atmosphere. After stirring at room temperature for 12 hours, the reaction was quenched by adding an aqueous ammonium chloride solution (5 mL) to the reaction solution. After removing water from an organic layer solution obtained by extracting three times with 5 mL of dichloromethane by adding anhydrous magnesium sulfate, the solution was concentrated by filtering. The concentrated reaction product was separated by silica gel column chromatography (hexane:EtOAc, 2:1) to obtain the compound of Chemical Formula 3, dimethyl 2,5-bis(3,5-dimethoxy-4-(methoxymethoxy)phenyl)tetrahydrofuran-3,4-dicarboxylate, as a yellow liquid (476 mg, 0.819 mmol, 99% yield).

IR (neat): 2983 (w), 1735 (s), 1365 (m), 1240 (s), 1045 (s), 920 (m), 732 (s) $cm^{-1}$.

$^1$H NMR (CDCl$_3$, 400 MHz): δ 6.68 (s, 4H), 5.38 (d, J=2.5 Hz, 1H), 5.36 (d, J=2.5 Hz, 1H), 5.13 (s, 4H), 3.87 (s, 12H), 3.74 (s, 6H), 3.61 (s, 6H), 3.60 (d, J=2.4 Hz, 2H).

$^{13}$C NMR (CDCl$_3$, 100 MHz): δ 171.5, 153.3, 135.9, 133.9, 102.5, 97.9, 82.9, 56.8, 56.2, 55.8, 52.3.

HRMS (ESI-TOF) m/z: [M+Na]$^+$ Calcd for $C_{28}H_{36}NaO_{13}$ 603.2054; Found 603.2059.

PREPARATION EXAMPLE 2

Synthesis of Compound of Chemical Formula 4 (2,5-bis(3,5-dimethoxy-4-(methoxymethoxy)phenyl) tetrahydrofuran-3,4-diyl)dimethanol)

After putting the MOM protecting group-introduced methyl ester compound of Chemical Formula 3 (50.0 mg, 0.0861 mmol) in a 10 mL round-bottom flask and adding toluene (1.9 mL) under a nitrogen atmosphere, diisobutylaluminum hydride (DIBAL-H) (420 µL, 0.419 mmol) was added. After stirring at room temperature for 1 hour and quenching remaining aluminum hydride by slowly adding 3 mL of an aqueous potassium sodium tartrate solution to the prepared reaction solution, the solution was washed three times with ethyl acetate (3 mL×3). After combining the organic layer solution and removing water with anhydrous magnesium sulfate, the solution was concentrated by filtering. The concentrated reaction product was separated by silica gel column chromatography ($CH_2Cl_2$:MeOH, 4:1) to obtain the alcohol compound of Chemical Formula 4, 2,5-bis(3,5-dimethoxy-4-(methoxymethoxy)phenyl)tetrahydrofuran-3,4-diyl)dimethanol, as a colorless liquid (43.0 mg, 0.0827 mmol, 96% yield).

IR (neat): 3392 (br s), 2940 (w), 1591 (m), 1227 (m), 1114 (s), 957 (s), 838 (w) $cm^{-1}$.

$^1$H NMR ($CDCl_3$, 400 MHz): δ 6.61 (s, 4H), 5.12 (s, 4H), 4.78 (d, J=8.8 Hz, 2H), 3.87 (s, 12H), 3.86-3.82 (m, 2H), 3.71-3.63 (m, 2H), 3.60 (s, 6H), 3.40 (br s, 2H), 2.35-2.26 (m, 2H).

$^{13}$C NMR ($CDCl_3$, 100 MHz): δ 153.6, 137.8, 134.3, 103.3, 98.2, 83.4, 63.0, 57.1, 56.7, 56.2.

HRMS (ESI-TOF) m/z: $[M+Na]^+$ Calcd for $C_{26}H_{36}NaO_{11}$ 547.2155; Found 547.2158.

PREPARATION EXAMPLE 3

Synthesis of Compound of Chemical Formula 6 ((2E,2'E)-2,5-bis(3,5-dimethoxy-4-(methoxymethoxy)phenyl)tetrahydrofuran-3,4-diyl) bis(methylene)bis(3-(4-(methoxymethoxy)phenyl) acrylate))

After adding the compound of Chemical Formula 4 substituted with two alcohol groups (580 mg, 1.11 mmol), the trans-coumaric acid derivative compound of Chemical Formula 5 (575 mg, 2.76 mmol), DMAP (4-dimethylaminopyridine, 405 mg, 3.32 mmol) and EDC (N-(3-dimethylaminopropyl)-N-ethylcarbodiimide hydrochloride, 529 mg, 2.76 mmol) to a 100-mL round-bottom flask and lowering reaction temperature to 0° C. under a nitrogen atmosphere, 61 mL of dichloromethane was added. After stirring at 0° C. for 1 hour, the temperature was raised to room temperature and stirring was performed further for 2 hours. After adding an aqueous ammonium chloride solution (60 mL) to the reaction mixture solution, the solution was washed three times with 60 mL of dichloromethane. After combining the organic layer solution and removing water with anhydrous magnesium sulfate, the solution was concentrated by filtering. The concentrated reaction product was separated by silica gel column chromatography (hexane:$Et_2O$:$CH_2Cl_2$, 1:1:1) to obtain the ester compound of Chemical Formula 6, (2E,2'E)-2,5-bis(3,5-dimethoxy-4-(methoxymethoxy)phenyl)tetrahydrofuran-3,4-diyl)bis(methylene) bis(3-(4-(methoxymethoxy)phenyl) acrylate), as a white solid (724 mg, 0.800 mmol, 72% yield).

IR (neat): 2990 (w), 1760 (m), 1597 (m), 1509 (m), 1240 (s), 1146 (s), 970 (s), 832 (m), 757 (w) $cm^{-1}$.

$^1$H NMR ($CDCl_3$, 400 MHz): δ 7.61 (d, J=15.9 Hz, 2H), 7.44 (d, J=8.8 Hz, 4H), 7.03 (d, J=8.8 Hz, 4H), 6.70 (s, 4H), 6.28 (d, J=15.9 Hz, 2H), 5.21 (s, 4H), 5.13 (s, 4H), 5.04-5.03 (m, 2H), 4.44-4.43 (m, 4H), 3.86 (s, 12H), 3.61 (s, 6H), 3.49 (s, 6H), 2.65-2.60 (m, 2H).

$^{13}$C NMR ($CDCl_3$, 100 MHz): δ 167.0, 159.2, 153.5, 145.2, 137.5, 133.8, 129.8, 127.8, 116.4, 115.1, 102.7, 98.1, 94.0, 83.0, 63.5, 57.1, 56.1, 56.0, 50.4.

HRMS (ESI-TOF) m/z: $[M+Na]^+$ Calcd for $C_{48}H_{56}NaO_{17}$ 927.3415; Found 927.3416.

PREPARATION EXAMPLE 4

Synthesis of Compound of Chemical Formula 7 (2E,2'E)-(-2,5-bis(4-hydroxy-3,5-dimethoxyphenyl) tetrahydrofuran-3,4-diyl)bis(methylene)bis(3-(4-hydroxyphenyl)acrylate)

After putting the MOM protecting group-introduced compound of Chemical Formula 6 (212 mg, 0.234 mmol) in a 25-mL round-bottom flask and adding methanol (7 mL) and 12 N HCl (0.8 mL), the mixture was stirred at 50° C. for 5 minutes. After the reaction, a reaction product remaining after concentrating the solvent was separated by silica gel column chromatography (EtOAc:$CH_2Cl_2$, 1:1) to obtain the final product compound of Chemical Formula 7 ((2E,2'E)-(-2,5-bis(4-hydroxy-3,5-dimethoxyphenyl)tetrahydrofuran-3,4-diyl)bis(methylene) bis(3-(4-hydroxyphenyl) acrylate) as a yellow solid (119 mg, 0.163 mmol, 70% yield). The compound of Chemical Formula 7 was named 'NK11' or 'orizativol A' by the inventors of the present disclosure.

IR (neat): 3385 (br s), 2990 (w), 2363 (w), 1710 (m), 1597 (m), 1503 (m), 1233 (s), 1146 (s), 970 (s), 832 (m), 751 (w) $cm^{-1}$.

$^1$H NMR ($CD_3OD$, 400 MHz): δ 7.39 (d, J=15.9 Hz, 2H), 7.36 (d, J=8.8 Hz, 4H), 6.80-6.74 (m, 8H), 6.21 (d, J=15.9 Hz, 2H), 5.04 (d, J=8.3 Hz, 2H), 4.45-4.37 (m, 4H), 3.82 (s, 12H), 2.70-2.63 (m, 2H).

$^{13}$C NMR ($CD_3OD$, 100 MHz): δ 169.1, 161.6, 149.6, 147.2, 136.7, 133.8, 131.5, 127.2, 117.1, 115.0, 105.2, 85.8, 64.8, 57.0, 51.8.

HRMS (ESI-TOF) m/z: $[M+Na]^+$ Calcd for $C_{40}H_{40}NaO_{13}$ 751.2367; Found 751.2362.

PREPARATION EXAMPLE 5

Synthesis of Compound of Chemical Formula 8

The compound of Chemical Formula 8 was synthesized by binding the trans-coumaric acid derivative compound of Chemical Formula 5 (a derivative wherein a MOM protecting group is bonded to the hydroxy group of 4-hydroxycinnamic acid) and its isomer, cis-coumaric acid derivative (a derivative wherein a MOM protecting group is bonded to the hydroxy group of cis-4-hydroxycinnamic acid) to a tetrahydrofuran ring using the methods of Preparation Examples 3 and 4. The compound of Chemical Formula 8 was named 'orizativol B' by the inventors of the present disclosure.

PREPARATION EXAMPLE 6

Synthesis of Compound of Chemical Formula 9

The compound of Chemical Formula 9 was synthesized using trans-cinnamic acid instead of the trans-coumaric acid derivative compound of Chemical Formula 5 (a derivative wherein a MOM protecting group is bonded to the hydroxy group of 4-hydroxycinnamic acid) using the methods of Preparation Examples 3 and 4.

PREPARATION EXAMPLE 7

Synthesis of Compound of Chemical Formula 10

The compound of Chemical Formula 10 was synthesized by binding an acetoxymethyl group to a tetrahydrofuran ring using the methods of Preparation Examples 3 and 4.

[Chemical Formula 10]

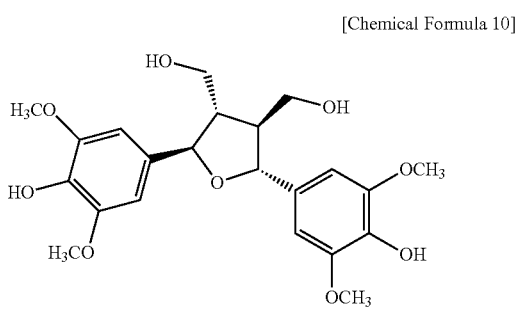 [SMILES: COc1cc([C@@H]2O[C@@H](c3cc(OC)c(O)c(OC)c3)[C@H](CO)[C@H]2CO)cc(OC)c1O]

PREPARATION EXAMPLE 8

Synthesis of Compound of Chemical Formula 11 (2,5-bis(3,5-dimethoxy-4-(methoxymethoxy)phenyl) tetrahydrofuran-3,4-diyl)diacetate)

The compound of Chemical Formula 11 was synthesized by binding a hydroxymethyl group to a tetrahydrofuran ring using the methods of Preparation Examples 3 and 4.

[Chemical Formula 11]

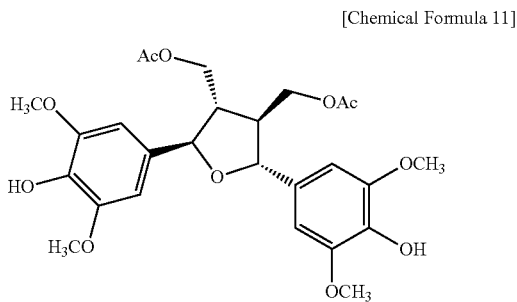 [SMILES: COc1cc([C@@H]2O[C@@H](c3cc(OC)c(O)c(OC)c3)[C@H](COC(C)=O)[C@H]2COC(C)=O)cc(OC)c1O]

TEST EXAMPLE 1

Measurement of Activity of Promoting Osteoblast Differentiation and Inhibiting Adipocyte Differentiation of NK11 Compound (1) Measurement of Activity of Promoting ALP (Alkaline Phosphatase) Production of NK11 Compound The C3H10T1/2 cells derived from mouse embryo fibroblasts are pluripotent stem cells that can differentiate into various cell lineages including osteoblasts. Because one of the characteristics of osteoblasts is the ALP (alkaline phosphatase) activity, the differentiation of the C3H10T1/2 cells into osteoblasts was measured based on the ALP activity.

Figure 3:
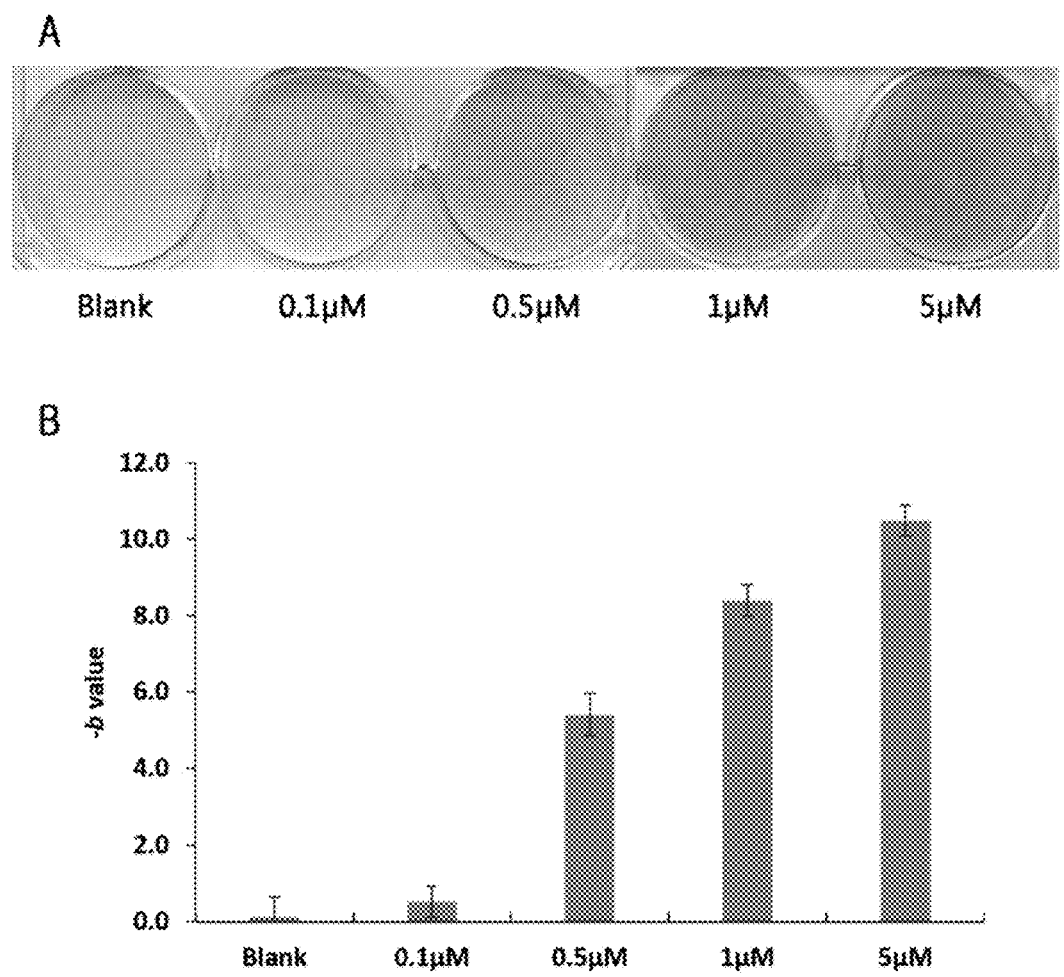
FIG. 3 shows a result of comparing the change in ALP (alkaline phosphatase) production during differentiation of C3H10T1/2 cells into osteoblasts depending on treatment with the NK11 compound with ALP staining images as well as the -b value as a measure of the change in ALP production in Test Example 1.

The C3H10T1/2 cells were cultured with a DMEM medium supplemented with 10% FBS and 1% penicillin/streptomycin under the condition of 37° C. and 5% $CO_2$. The C3H10T1/2 cells were cultured on a 6-well plate at a concentration of $2.5 \times 10^4$/mL with a medium containing 10 mM β-glycerophosphate and 50 μg/mL ascorbic acid for osteocyte differentiation. The differentiation was performed for 9 days after adding the NK11 compound at 0.1, 0.5, 1 and 5 μM, while replacing the medium with 3-day intervals. Then, ALP staining was performed using 5-bromo-4-chloro-3-indolyl phosphate/nitro blue tetrazolium (BCIP/NBT). The result is shown in FIG. 3.

Then, the Lab color space was measured using the image files of the ALP-stained well plate. The NK11 compound increased ALP production in a concentration-dependent manner as compared to a DMSO-treated negative control group (blank) (see FIG. 3).

Figure 4:
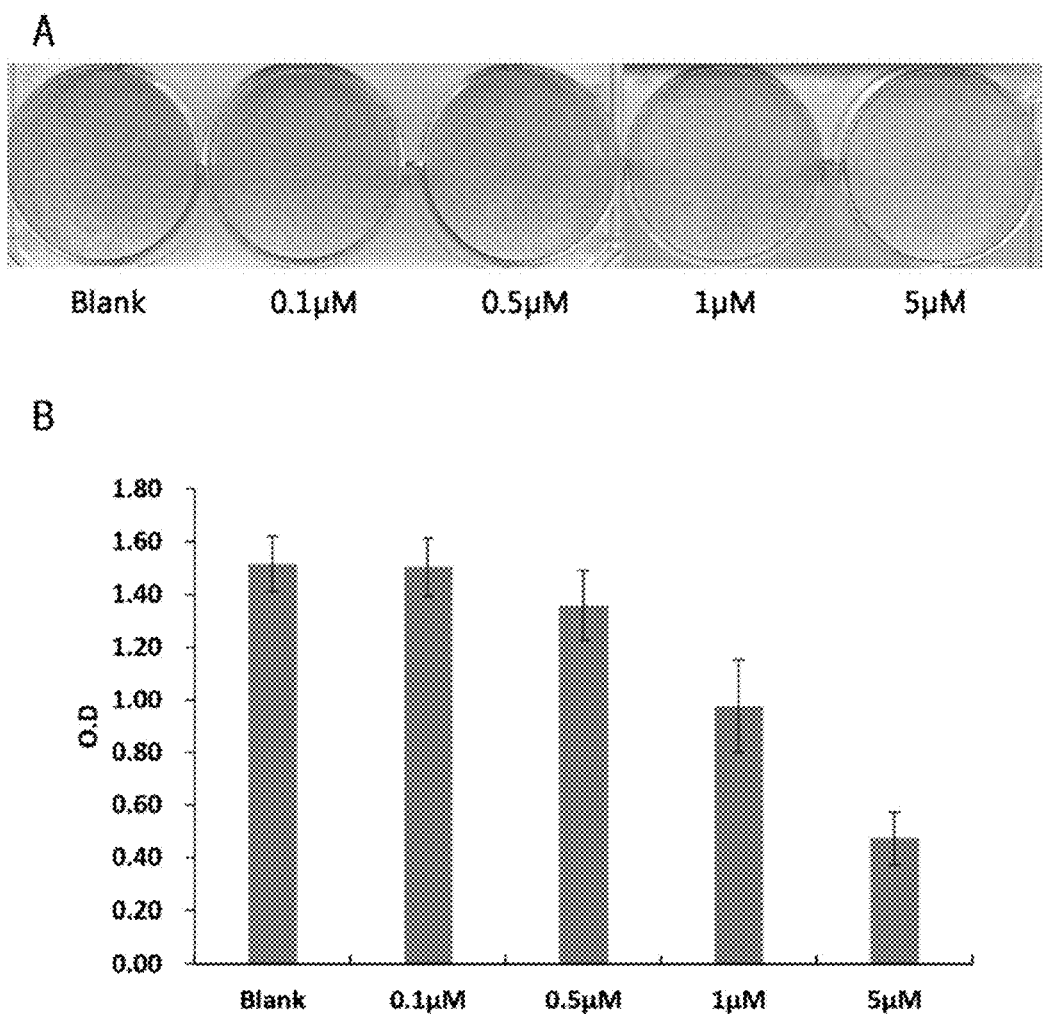
FIG. 4 shows a result of comparing the change in fat production during differentiation of C3H10T1/2 cells into adipocytes depending on treatment with the NK11 compound with Oil Red O staining as well as Oil Red O absorbance in Test Example 1.

(2) Measurement of Activity of Inhibiting Adipocyte Differentiation of NK11 Compound After plating the cells on a 6-well plate in the same manner as in Test Example 1, they were cultured for 9 days in a medium containing 1 μM dexamethasone, 5 μg/mL insulin and 1 μM troglitazone for adipocyte differentiation after adding the NK11 compound at 0.1, 0.5, 1 and 5 μM. After completion of differentiation, the medium was removed and the cells were fixed with 10% neutral buffered formalin and stained with 0.5% Oil Red O solution. The result is shown in FIG. 4.

Then, the Lab color space was measured using the image files of the Oil Red O-stained well plate. The NK11 compound inhibit fat production by adipocytes in a concentration-dependent manner as compared to a DMSO-treated negative control group (blank) (see FIG. 4).

(3) Measurement of Expression Levels of Osteoblast Differentiation Factor and Adipocyte Differentiation Factor The mRNA expression levels of the osteoblast differentiation factor and the adipocyte differentiation factor in the cells treated with the NK11 compound were investigated. The result is shown in FIG. 5.

First, the expression level of the osteoblast differentiation factor ALP was investigated while differentiating the C3H10T1/2 cells into osteoblasts in the same manner as in Test Example 1. Also, the expression levels of the adipocyte differentiation factors PPARγ, aP2 and CD36 compound were investigated while differentiating the C3H10T1/2 cells into adipocytes in the same manner as in Test Example 1.

Total RNA was extracted using TRIzol (Invitrogen). 1 μg of the isolated RNA was synthesized into cDNA by adding random primers, dNTP and PrimeScript™ reverse transcriptase (Takara). The synthesized cDNA was subjected to real-time PCR using primers and SYBR Premix Ex Taq (Takara).

Figure 5:
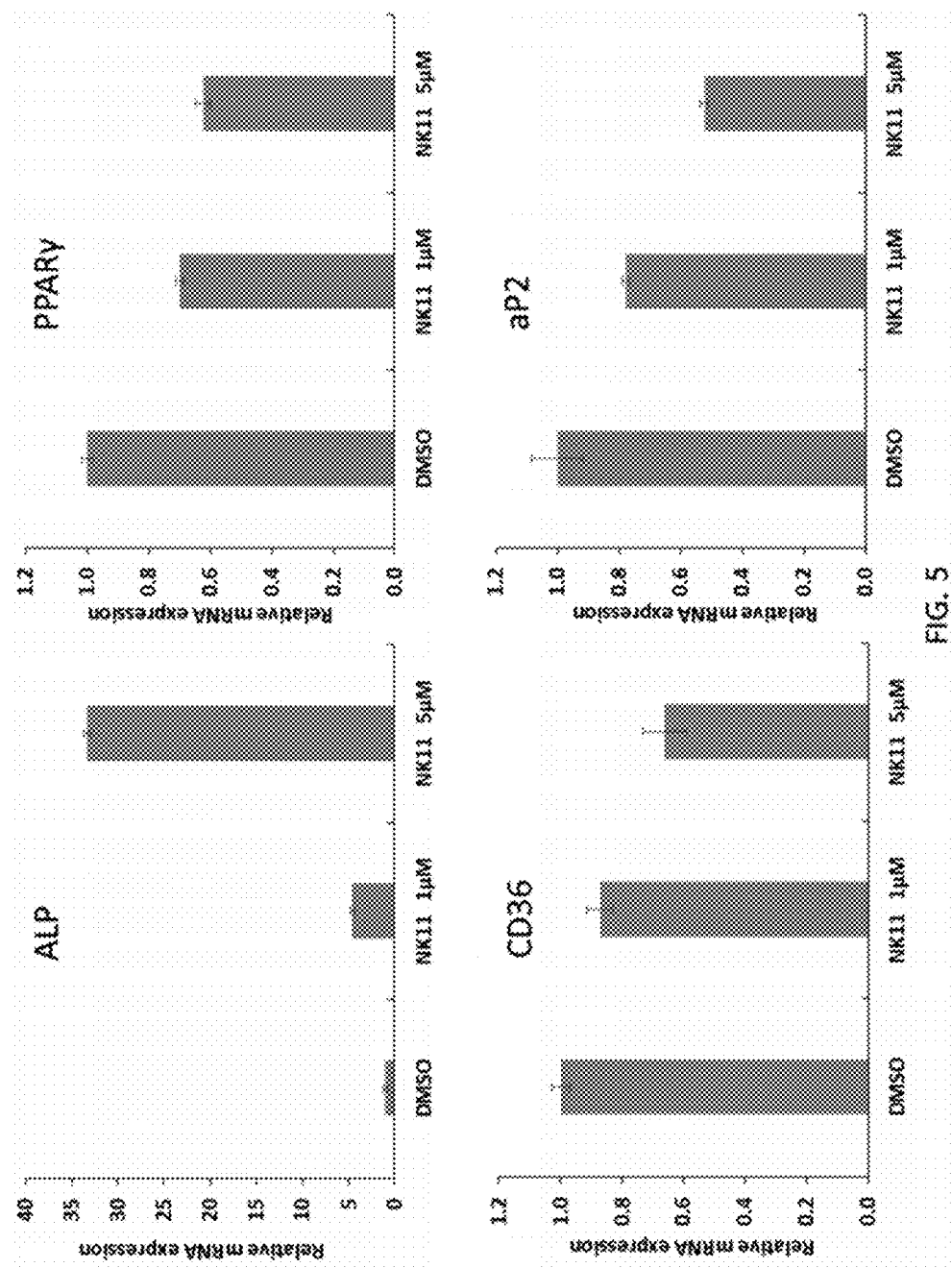
FIG. 5 shows the change in the expression of PPARγ, aP2, CD36 and ALP mRNAs in C3H10T1/2 cells depending on treatment with the NK11 compound in Test Example 1.

The expression levels of the adipocyte-related genes CD36, aP2 and PPARγ were decreased in a concentration-dependent manner and ALP, which is an important osteogenesis marker, was expressed highly at the concentration of 5 μM (see FIG. 5).

TEST EXAMPLE 2

Comparison of Activity of Promoting Osteoblast Differentiation and Inhibiting Adipocyte Differentiation of NK11 Compound and Compound of Chemical Formula 8

The NK11 compound has two trans-coumaric acid derivative compounds bound to the 3- and 4-positions of the tetrahydrofuran ring and the compound of Chemical Formula 8 is an isomer of the NK11 compound with one of the trans-coumaric acid derivatives on the furan ring replaced by a cis-coumaric acid derivative.

The activity of promoting osteoblast differentiation and inhibiting adipocyte differentiation of the compound of Chemical Formula 8, which is an isomer of the NK11 compound, was compared in the same manner as in Test Example 1.

(1) Comparison of Activity of Promoting ALP (Alkaline Phosphatase) Production of NK11 Compound and Compound of Chemical Formula 8

Figure 6:
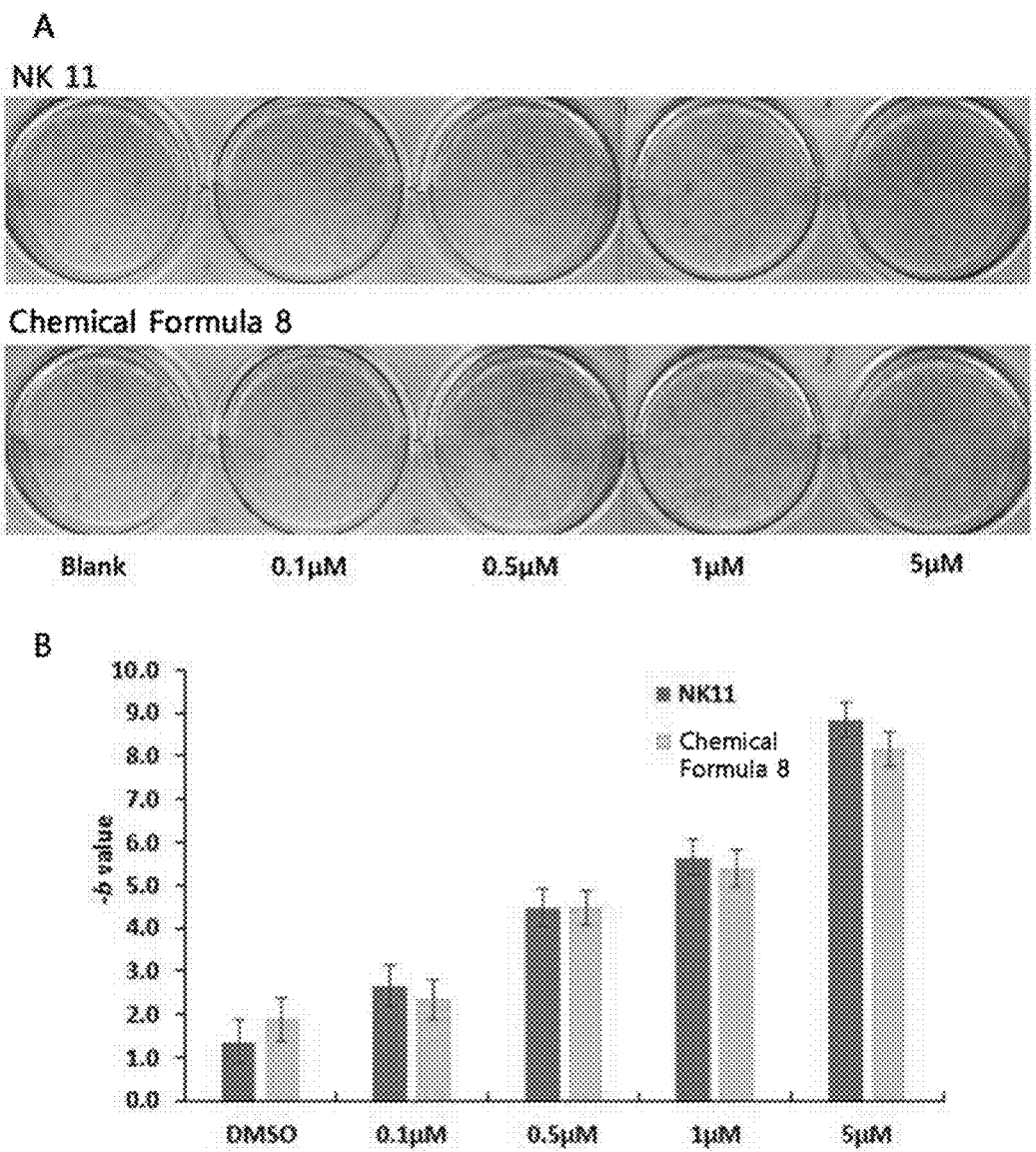
FIG. 6 shows a result of comparing the change in ALP (alkaline phosphatase) production during differentiation of C3H10T1/2 cells into osteoblasts depending on treatment with the NK11 compound and the compound of Chemical Formula 8 with ALP staining images as well as the -b value as a measure of the change in ALP production in Test Example 2.

As seen from the ALP staining images and graph in FIG. 6, the compound of Chemical Formula 8 increased ALP production in a concentration-dependent manner like the NK11 compound.

(2) Comparison of Activity of Inhibiting Adipocyte Differentiation of NK11 Compound and Compound of Chemical Formula 8

Figure 7:
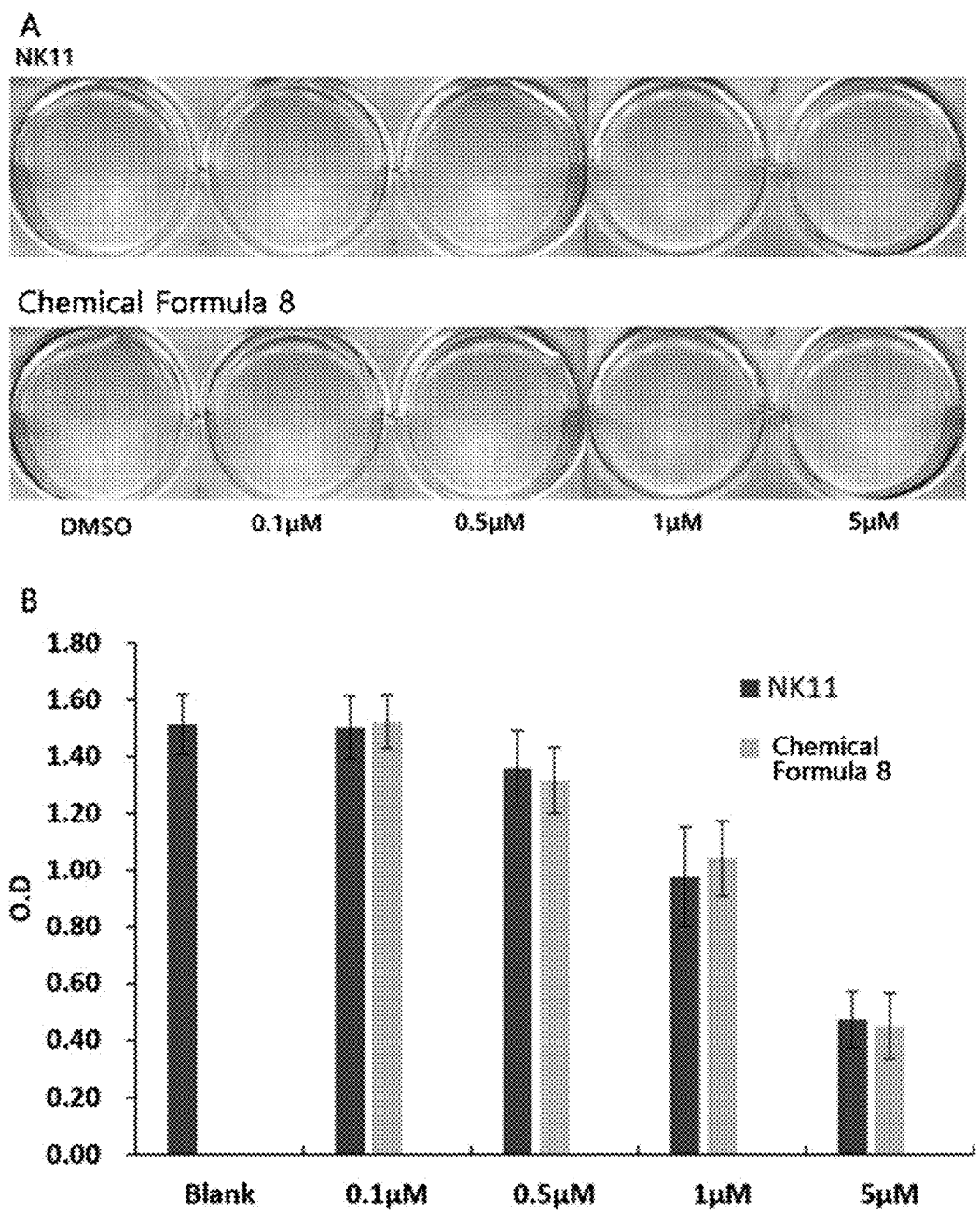
FIG. 7 shows a result of comparing the change in fat production during differentiation of C3H10T1/2 cells into osteoblasts depending on treatment with the NK11 compound and the compound of Chemical Formula 8 with Oil Red O staining as well as Oil Red O absorbance in Test Example 2.

As seen from the images and graph in FIG. 7, the compound of Chemical Formula 8 inhibited fat production by adipocytes in a concentration-dependent manner like the NK11 compound and the effect depending on concentration was almost the same as that of the NK11 compound.

Figure 8:
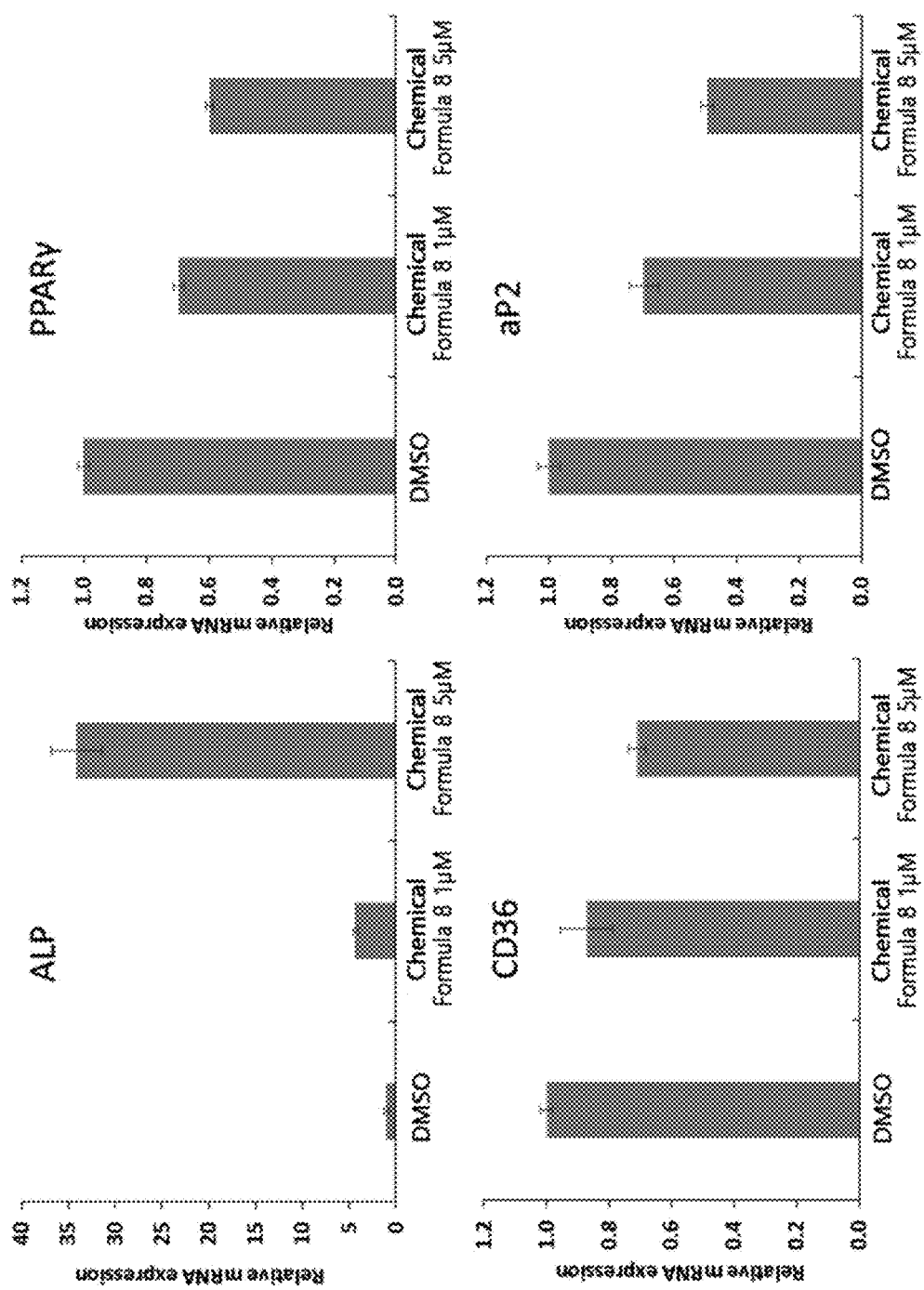
FIG. 8 shows the change in the expression of PPARγ, aP2, CD36 and ALP mRNAs in C3H10T1/2 cells depending on treatment the compound of Chemical Formula 8 in Test Example 2.

(3) Comparison of Expression Levels of Osteoblast Differentiation Factor and Adipocyte Differentiation Factor As seen from FIG. 8, the compound of Chemical Formula 8 decreased the expression levels of the adipocyte-related genes CD36, aP2 and PPARγ in a concentration-dependent manner like the result for the NK11 compound shown in FIG. 5 and ALP, which is an important osteogenesis marker, was expressed highly at the concentration of 5 μM.

TEST EXAMPLE 3

Comparison of Activity of Promoting Osteoblast Differentiation and Inhibiting Adipocyte Differentiation of NK11 Compound and Compounds of Chemical Formula 4, Chemical Formula 2, Chemical Formula 10, Chemical Formula 11 and Chemical Formula 9

The compounds of Chemical Formula 4 and Chemical Formula 11 have two hydroxymethyl groups bound to the 3- and 4-positions of the tetrahydrofuran ring. For the compound of Chemical Formula 4, a methoxymethyl protecting group is bound to the hydroxy group of the 4-position of the phenyl group bonded to the 2- and 5-positions of the tetrahydrofuran ring, whereas, for the compound of Chemical Formula 11, the hydroxy group is exposed without being protected.

The compound of Chemical Formula 2 has two methylcarboxyl groups bound to the 3- and 4-positions of the tetrahydrofuran ring and the compound of Chemical Formula 10 has two acetoxymethyl groups bound to the 3- and 4-positions of the tetrahydrofuran ring.

And, the compound of Chemical Formula 9 has two cinnamic acids bound to the 3- and 4-positions of the tetrahydrofuran ring instead of the trans-coumaric acid derivatives.

In Test Example 3, the activity of promoting osteoblast differentiation and inhibiting adipocyte differentiation of the intermediates during the synthesis of the NK11 compound and the compounds having similar structures as the NK11 compound was compared with that of NK11 compound by the same method as in Test Example 1. The NK11 compound was treated at 1 μM and other compounds were treated at 5 μM.

(1) Comparison of Activity of Promoting ALP (Alkaline Phosphatase) Production

Figure 9:
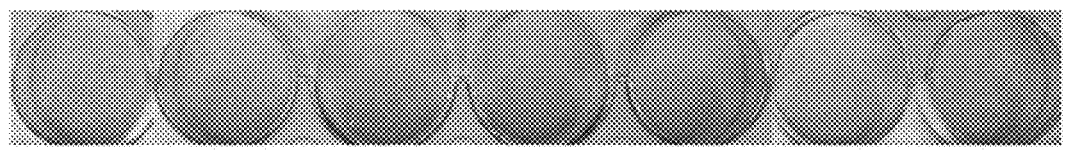
FIG. 9 shows a result of comparing the change in ALP (alkaline phosphatase) production during differentiation of C3H10T1/2 cells into osteoblasts depending on treatment with the NK11 compound and the compounds of Chemical Formula 4, Chemical Formula 2, Chemical Formula 10, Chemical Formula 11 and Chemical Formula 9 with ALP staining images as well as the –b value as a measure of the change in ALP production in Test Example 3.
Figure 9:
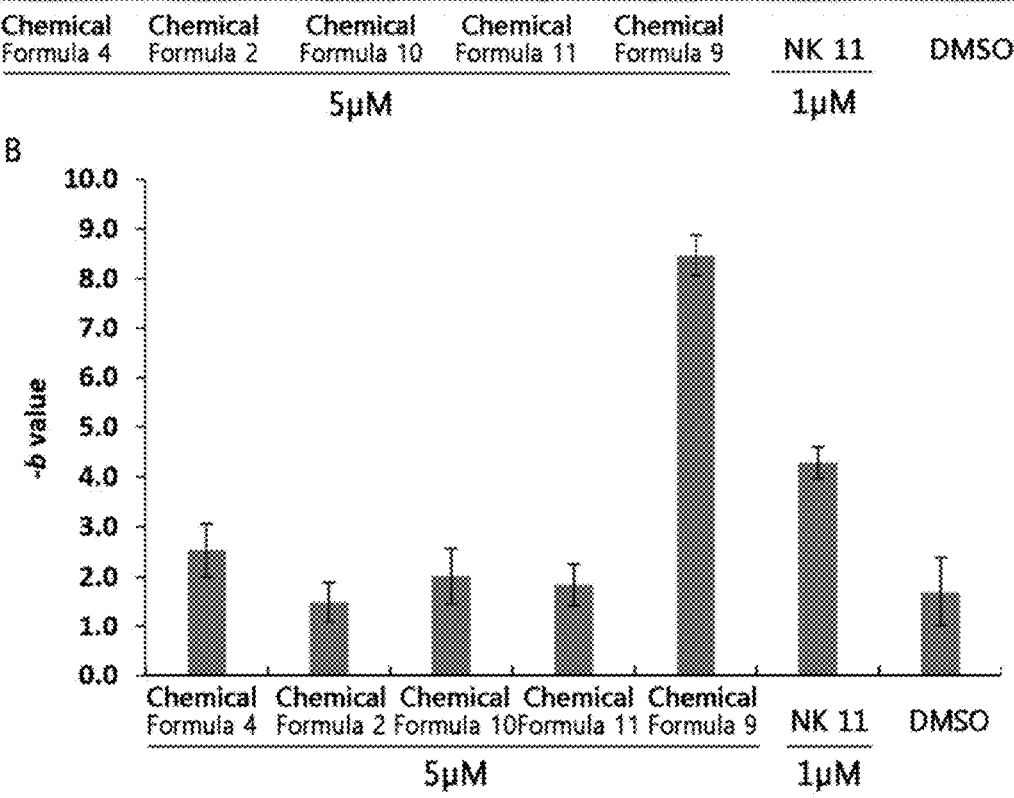

The intermediates during the synthesis of the NK11 compound and the compounds having similar structures, i.e., the compounds of Chemical Formula 4, Chemical Formula 2, Chemical Formula 10 and Chemical Formula 11, showed no difference in ALP production from the negative control group (DMSO) and only the compound of Chemical Formula 9 showed about 2 times of ALP production as compared to the NK11 compound (see FIG. 9). When considering the concentrations of the NK11 compound and the compound of Chemical Formula 9 used in the experiment, it can be seen that the compound of Chemical Formula 9 has a significant effect of promoting ALP production although slightly lower than that of NK11.

(2) Comparison of Activity of Inhibiting Adipocyte Differentiation

Figure 10:
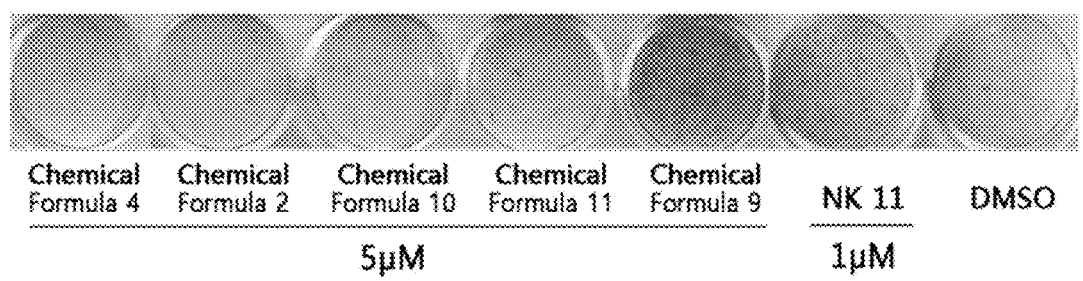
FIG. 10 shows a result of comparing the change in fat production during differentiation of C3H10T1/2 cells into adipocytes depending on treatment with the NK11 compound and the compounds of Chemical Formula 4, Chemical Formula 2, Chemical Formula 10, Chemical Formula 11 and Chemical Formula 9 with Oil Red O staining as well as Oil Red O absorbance in Test Example 3.
Figure 10:
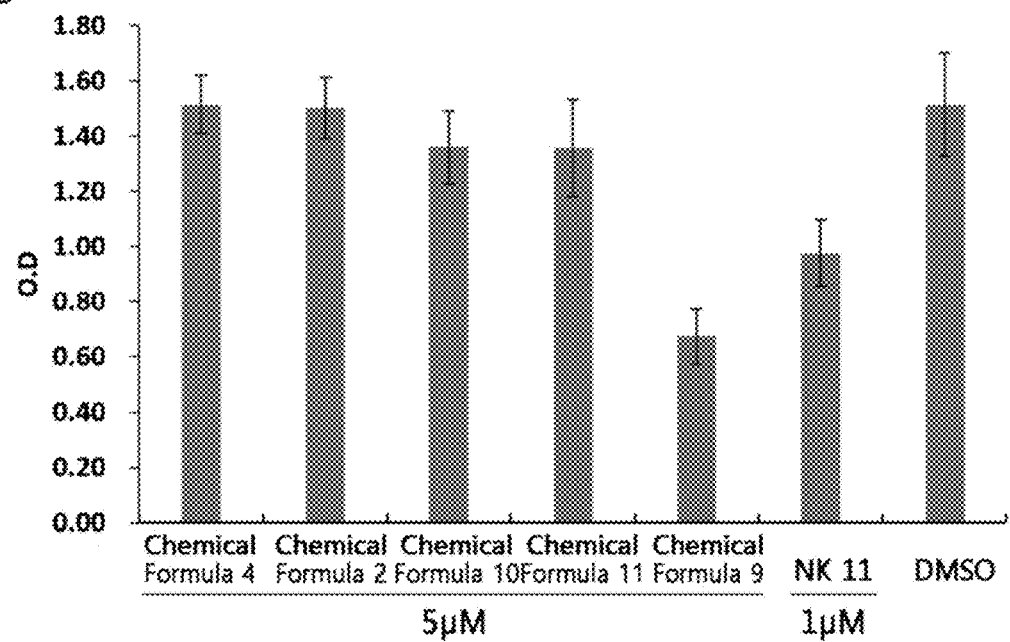

The compounds of Chemical Formula 4, Chemical Formula 2, Chemical Formula 10 and Chemical Formula 11 had showed no difference in the effect of inhibiting adipocyte differentiation from the negative control group (DMSO) and only the compound of Chemical Formula 9 showed the effect of inhibiting adipocyte differentiation as the NK11 compound (see FIG. 10).

Figure 11:
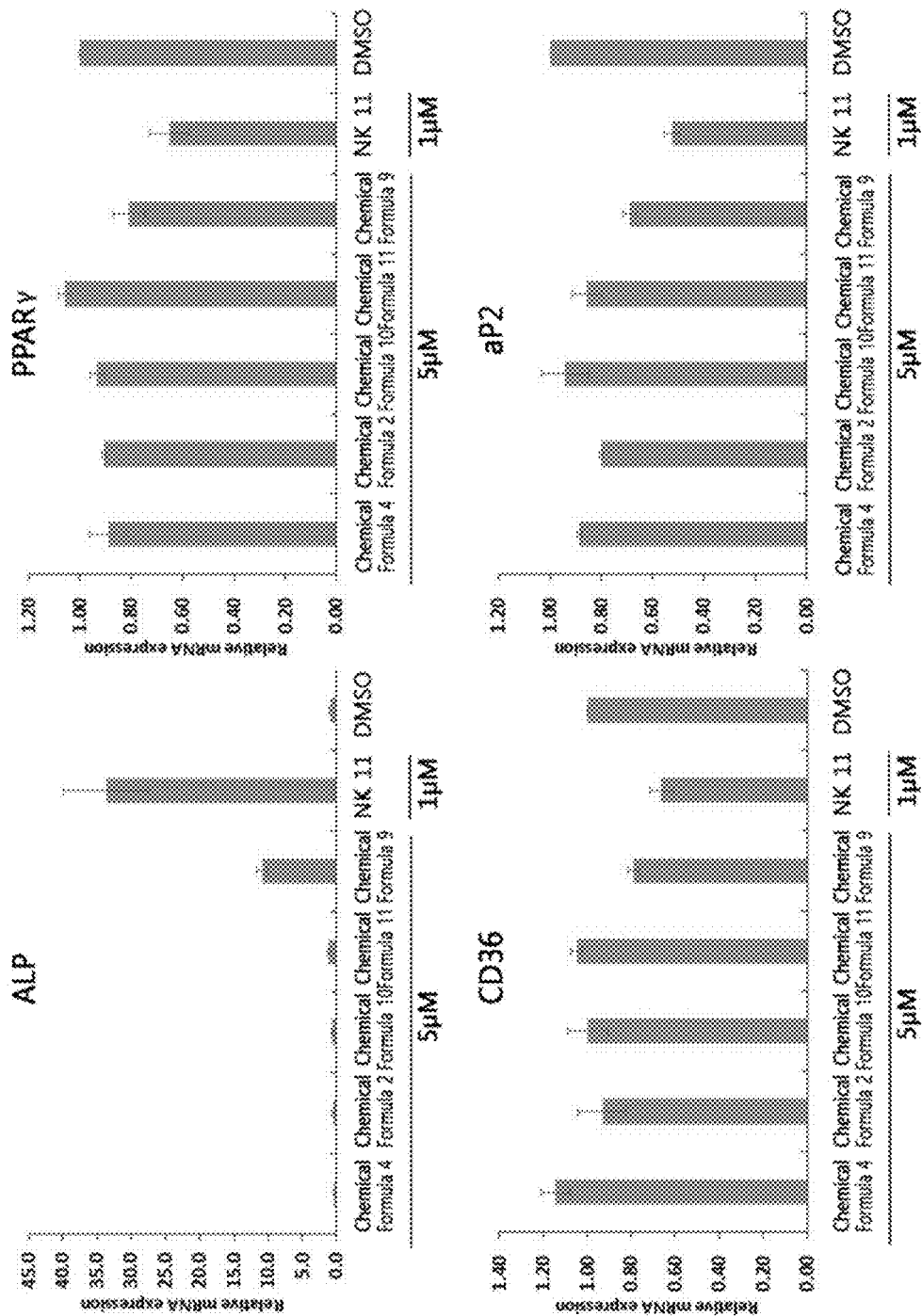
FIG. 11 shows the change in the expression of PPARγ, aP2, CD36 and ALP mRNAs in C3H10T1/2 cells depending on treatment the compounds of Chemical Formula 4, Chemical Formula 2, Chemical Formula 10, Chemical Formula 11 and Chemical Formula 9 in Test Example 3.

(3) Comparison of Expression Levels of Osteoblast Differentiation Factor and Adipocyte Differentiation Factor The compounds of Chemical Formula 4, Chemical Formula 2, Chemical Formula 10 and Chemical Formula 11 had no effect on the expression levels of the adipocyte-related genes CD36, aP2 and PPARγ or the expression level of ALP, which is an important osteogenesis marker (see FIG. 11).

However, the compound of Chemical Formula 9 decreased the expression levels of adipocyte-related genes CD36, aP2 and PPARγ like the NK11 compound and the expression level of ALP, which is an important osteogenesis marker, was high. But, although the compound of Chemical Formula 9 was treated with 5 times higher concentration than the NK11 compound, the group treated with the NK11 compound showed higher effect of inhibiting the expression of the adipocyte differentiation factors and promoting the expression of the osteoblast differentiation factor.

TEST EXAMPLE 4

Animal Experiment Using Ovariectomized Metabolic Bone Disease Animal Model

In order to investigate how the NK11 compound affects the treatment and prevention of metabolic bone disease, bone density measurement and histological analysis were conducted after administering the compound to ovariectomized white rats.

(1) Animal Breeding and Ovariectomy 8-week-old female SD (Sprague-Dawley) rats were purchased and accustomed for 1 week. Ovariectomy was conducted when the rats were 9 weeks old and they were allowed to recover for 1 week. The sample was orally administered once a day for 8 weeks. During the experiment period, each animal was housed in one cage and the environmental condition was adjusted to temperature 25±5° C., relative humidity 50±10% and 12 hr/12 hr light-dark cycles. Free access to feed (AlN-93g) and water was allowed.

The test groups consisted of a non-ovariectomized sham group, a group administered with distilled water after receiving ovariectomy (OVX), groups administered with 0.5 and 1mg/kg NK11 after receiving ovariectomy (NK11 0.5, NK11 1) and groups administered with 50 μg/kg estradiol and 50 mg/kg soy isoflavone as positive control groups.

After treating with the sample for 8 weeks, the rat was anesthetized with diethyl ether and blood was taken via cardiac puncture. The blood was left for 30 minutes and serum obtained by centrifuging at 3000 rpm for 10 minutes was used for biochemical analysis. Triglyceride, total cholesterol and ALP levels and GOT/GTP ratio were measured.

The body weight of the sacrificed ovariectomized white rat was measured and the BMD of the thighbone was measured using a dual-energy X-ray bone densitometer (Norland pDEXA).

The thighbone taken from the ovariectomized white rat was quick-frozen with liquid nitrogen and then pulverized for the measurement. Total RNA was extracted using TRIzol (Invitrogen). 1 μg of the isolated RNA was synthesized into cDNA by adding random primers, dNTP and PrimeScript™ reverse transcriptase (Takara). The synthesized cDNA was subjected to real-time PCR using primers and SYBR Premix Ex Taq (Takara) to investigate the expression level of the mRNA of ALP, which is an osteoblast differentiation factor.

(2) Measurement of Body Weight

Figure 12:
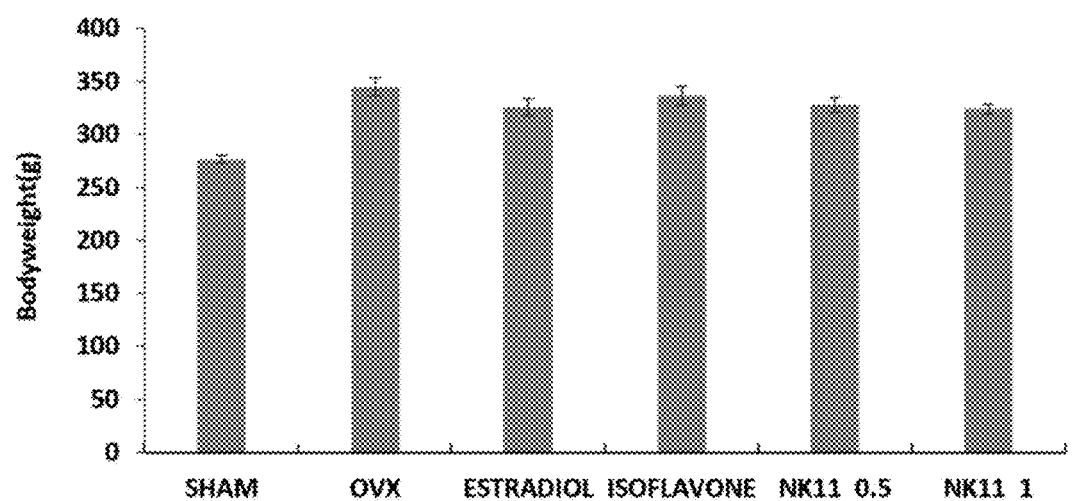
FIG. 12 shows a result of comparing the body weight of ovariectomized white rats orally administered with the NK11 compound for 8 weeks in Test Example 4.

All the ovariectomized test groups showed increased body weight as compared to the non-ovariectomized sham group. But, there was no significant difference (see FIG. 12).

(3) Measurement of Biochemical Indices

Figure 13:
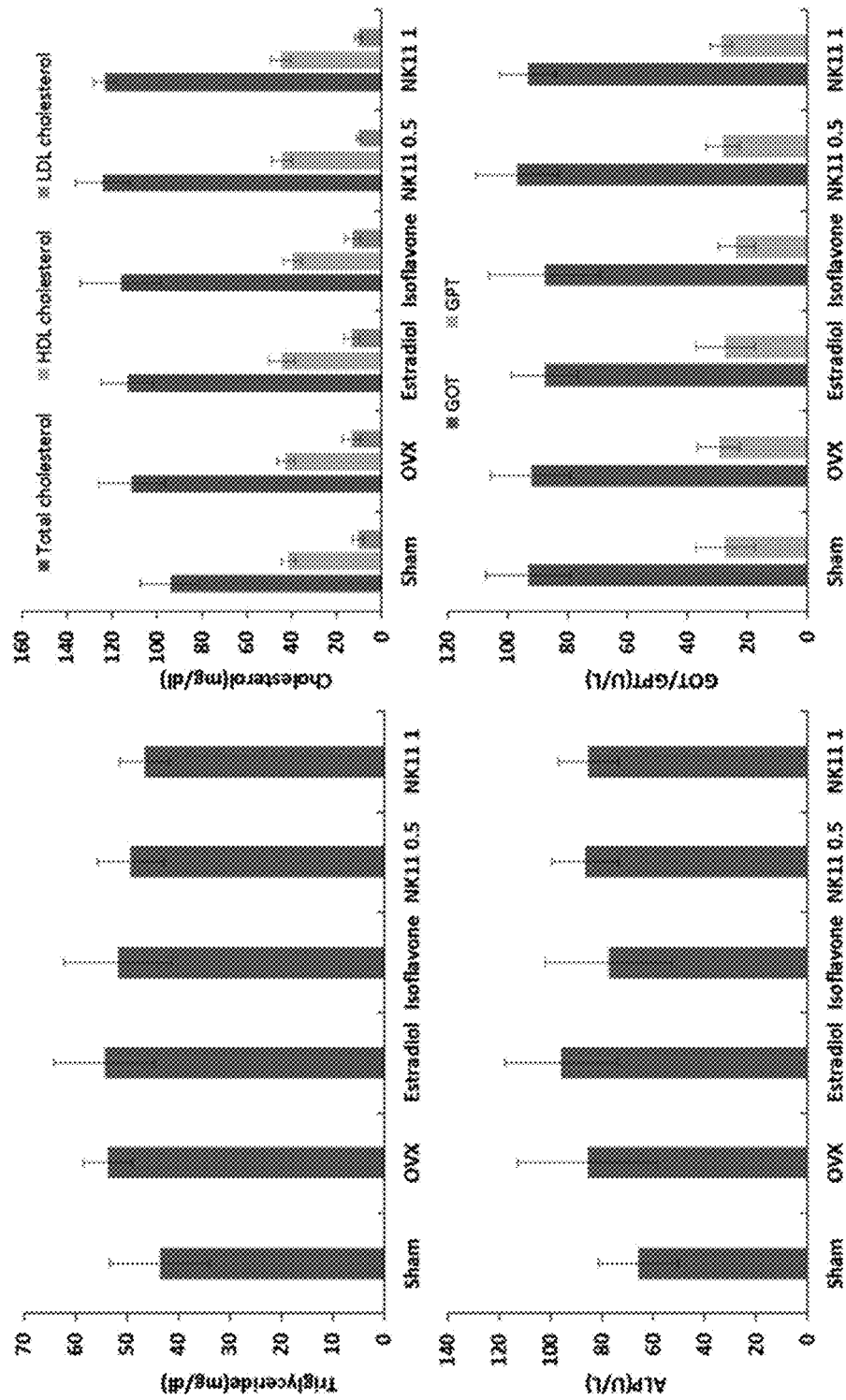
FIG. 13 shows a result of measuring triglyceride, cholesterol and ALP levels in the blood plasma of ovariectomized white rats administered with the NK11 compound in Test Example 4.

No significant difference in triglyceride, total cholesterol and ALP levels and GOT/GTP ratio was observed in all the test groups (see FIG. 13).

(4) Measurement of Bone Mineral Density (BMD)

Figure 14:
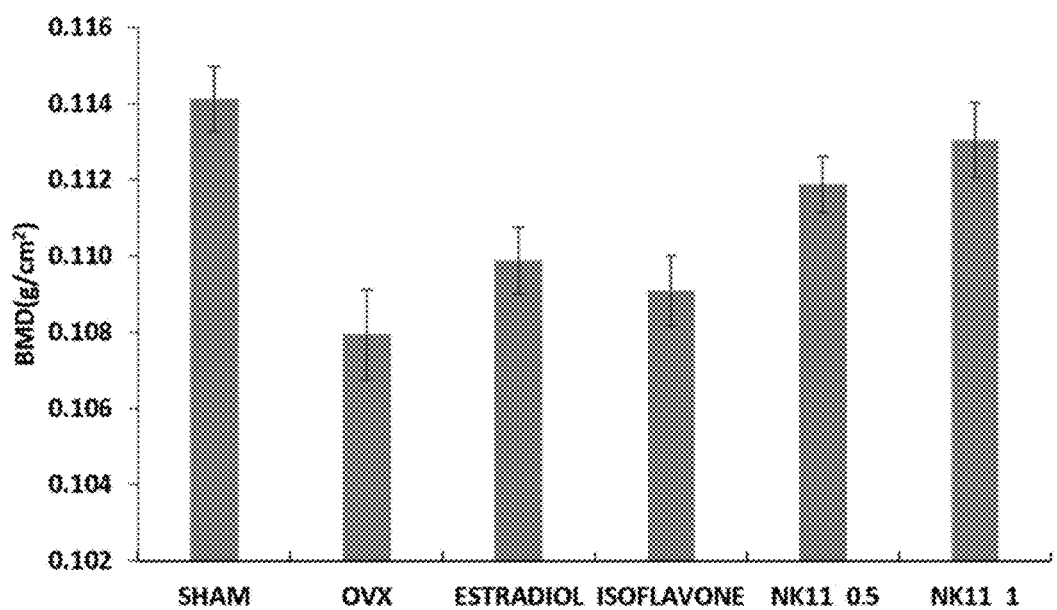
FIG. 14 shows a result of measuring the BMD of the thighbone of ovariectomized white rats administered with the NK11 compound in Test Example 4.

The ovariectomized test group (OVX) showed significant decrease in bone mineral density (BMD) as compared to the non-ovariectomized sham group. It was also found that the NK11 compound significantly increases bone density in a concentration-dependent manner as compared to the positive controls estradiol or soy isoflavone (see FIG. 14).

(5) Measurement of Expression Level of Osteoblast Differentiation Factor

Figure 15:
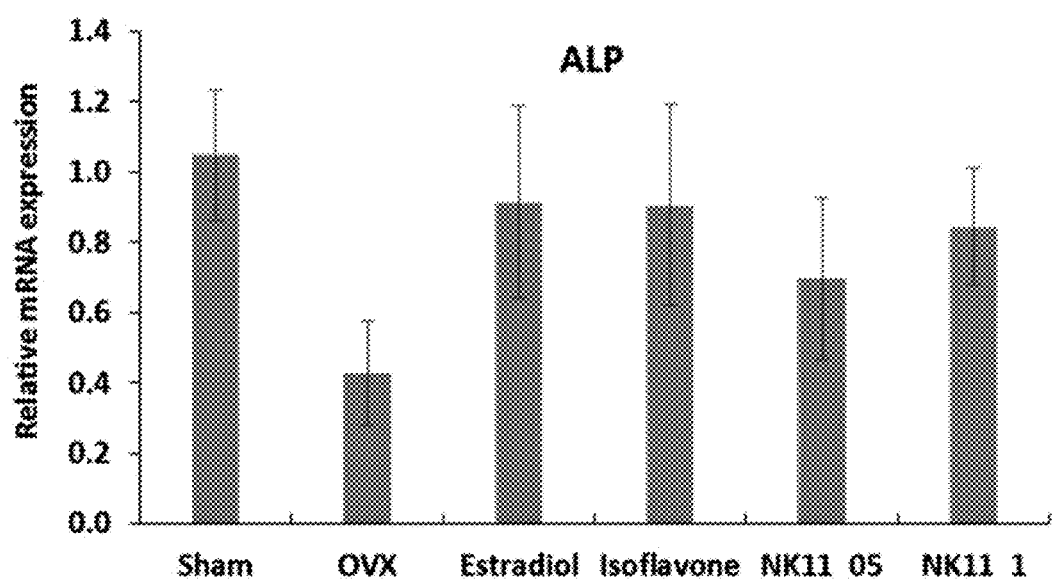
FIG. 15 shows a result of comparing the mRNA expression level in osteocytes in the thighbone of ovariectomized white rats administered with the NK11 compound in Test Example 4.

The expression level of the osteoblast differentiation factor ALP was significantly decreased in the ovariectomized test group (OVX) as compared to the non-ovariectomized sham group and was significantly increased again by the administration of the NK11 compound. The NK11 compound increased the expression level of ALP in a concentration-dependent manner and the expression level was comparable to that of the positive control groups at the concentration of 1 mg/kg (see FIG. 15).

Hereinafter, the present disclosure will be described in detail through formulation examples. However, they are for illustrative purposes only the present disclosure is not limited by them.

FORMULATION EXAMPLE 1

Preparation of Powder

| NK11 compound | 20 mg |
|---|---|
| Lactose | 100 mg |
| Talc | 10 mg |

A powder was prepared by mixing the above ingredients and filling in a sealed pouch.

FORMULATION EXAMPLE 2

Preparation of Tablet

| NK11 compound | 10 mg |
|---|---|
| Corn starch | 100 mg |
| Lactose | 100 mg |
| Magnesium stearate | 2 mg |

The above ingredients were mixed and prepared into a tablet according to a common tablet-making method.

FORMULATION EXAMPLE 3

Preparation of Capsule

| NK11 compound | 10 mg |
|---|---|
| Crystalline cellulose | 3 mg |
| Lactose | 14.8 mg |
| Magnesium stearate | 0.2 mg |

A capsule was prepared by mixing the above ingredients and filling in a gelatin capsule.

FORMULATION EXAMPLE 4

Preparation of Infection

| NK11 compound | 10 mg |
|---|---|
| Mannitol | 180 mg |
| Sterile distilled water for injection | 2974 mg |
| $Na_2HPO4 \cdot 12H_2O$ | 26 mg |

An injection was prepared by a common injection preparation method using the above ingredients per ampoule (2 mL).

FORMULATION EXAMPLE 5

Preparation of Liquid Formulation

| NK11 compound | 20 mg |
|---|---|
| High-fructose corn syrup | 10 g |
| Mannitol | 5 g |
| Purified water | Adequate |

The above ingredients were dissolved in purified water and an adequate amount of lemon flavor was added. After mixing the above ingredients and adjusting the total volume to 100 mL by adding purified water, the prepared liquid formulation was filled in a brown bottle and then sterilized.

FORMULATION EXAMPLE 6

Preparation of Health Functional Food

| NK11 compound | 1,000 mg |
|---|---|
| Vitamin mixture | Adequate |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Mineral mixture | Adequate |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |

| | |
|---|---|
| Potassium citrate | 90 mg |
| Calcium carbonate | 100 mg |
| Magnesium chloride | 24.8 mg |

The above contents of the vitamin and mineral mixtures are given as specific examples relatively suitable for health functional food but may be varied as desired. A health functional food was prepared by a common method after mixing the above ingredients and preparing into a granule.

FORMULATION EXAMPLE 7

Preparation of Health Functional Drink

| | |
|---|---|
| NK11 compound | 1,000 mg |
| Citric acid | 1,000 mg |
| Oligosaccharide | 100 g |
| Concentrated plum extract | 2 g |
| Taurine | 1 g |
| Purified water | To 900 mL |

According to a common health functional drink preparation method, the above ingredients were mixed and heated at 85° C. for about 1 hour under stirring. The resulting solution was filtered, collected in a sterilized 2-L container and stored in a refrigerator after sealing and sterilization for use in the preparation of the health functional drink of the present disclosure.

The above contents are given as specific examples relatively suitable for drink but may be varied as desired in consideration of regional and ethnic preferences such as consumer groups, countries, uses, etc.

The invention claimed is:

1. A composition comprising a compound of Chemical Formula 1, an isomer thereof or a pharmaceutically acceptable salt thereof as an active ingredient:

[Chemical Formula 1]

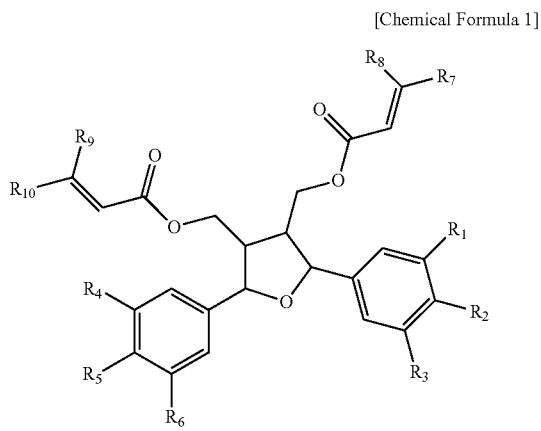

wherein each of $R_1$, $R_2$, $R_3$, $R_4$, $R_5$ and $R_6$, which may be identical or different from each other, is independently selected from a group consisting of hydrogen, hydroxy, $C_1$-$C_6$ alkyl, $C_1$-$C_6$ alkoxy, halogen and trifluoromethyl, and
wherein each of $R_7$, $R_8$, $R_9$ and $R_{10}$, which may be identical or different from each other, is independently hydrogen or phenyl, with the proviso that $R_8$ and $R_{10}$ are phenyl if $R_7$ and $R_9$ are hydrogen and $R_8$ and $R_{10}$ are hydrogen if $R_7$ and $R_9$ are phenyl and the phenyl is unsubstituted or substituted with a substituent selected from a group consisting of hydroxy, halogen and trifluoromethyl.

2. The composition according to claim 1, wherein each of $R_1$, $R_3$, $R_4$ and $R_6$, which may be identical or different from each other, is independently selected from a group consisting of $C_1$-$C_6$ alkyl and $C_1$-$C_6$ alkoxy, and
wherein each of $R_2$ and $R_5$, which may be identical or different from each other, is independently selected from a group consisting of hydrogen, hydroxy, halogen and trifluoromethyl.

3. The composition according to claim 2, wherein the compound of Chemical Formula 1 is a compound of Chemical Formula 7, Chemical Formula 8 or Chemical Formula 9:

[Chemical Formula 7]

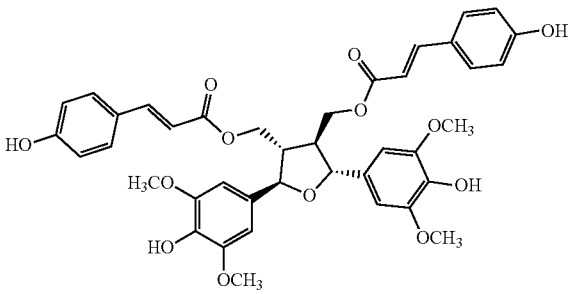

[Chemical Formula 8]

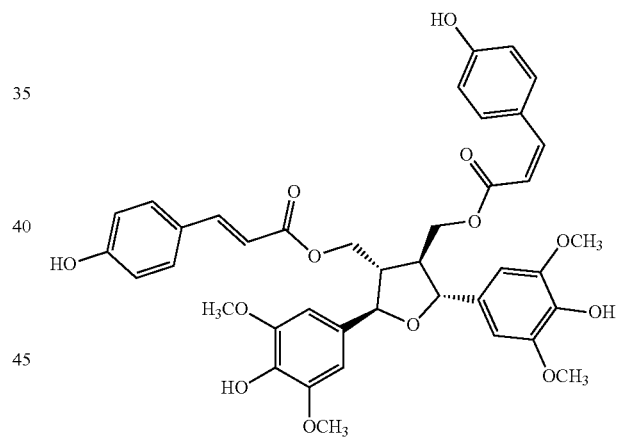

[Chemical Formula 9]

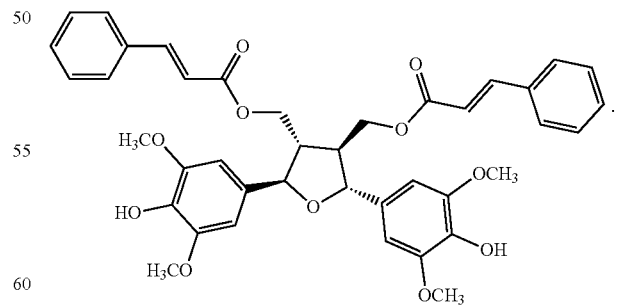

4. The composition according to claim 1, which promotes osteoblast differentiation and inhibits adipocyte differentiation.

5. The composition according to claim 4, which treats obesity and metabolic bone disease.

6. A health functional food comprising a compound of Chemical Formula 1, an isomer thereof or a pharmaceutically acceptable salt thereof as an active ingredient:

[Chemical Formula 1]

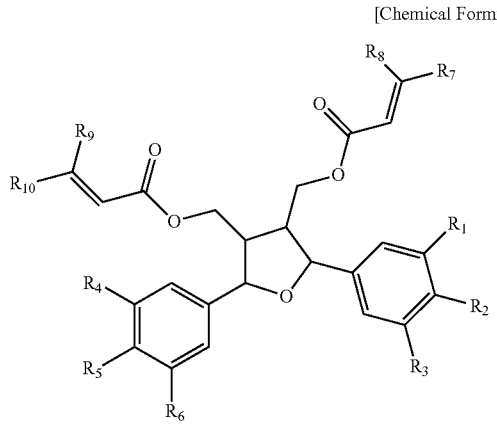

wherein each of $R_1$, $R_2$, $R_3$, $R_4$, $R_5$ and $R_6$, which may be identical or different from each other, is independently selected from a group consisting of hydrogen, hydroxy, $C_1$-$C_6$ alkyl, $C_1$-$C_6$ alkoxy, halogen and trifluoromethyl, and wherein each of $R_7$, $R_8$, $R_9$ and $R_{10}$, which may be identical or different from each other, is independently hydrogen or phenyl, with the proviso that $R_8$ and $R_{10}$ are phenyl if $R_7$ and $R_9$ are hydrogen and $R_8$ and $R_{10}$ are hydrogen if $R_7$ and $R_9$ are phenyl and the phenyl is unsubstituted or substituted with a substituent selected from a group consisting of hydroxy, halogen and trifluoromethyl.

7. The health functional food according to claim 6, wherein each of $R_1$, $R_3$, $R_4$ and $R_6$, which may be identical or different from each other, is independently selected from a group consisting of $C_1$-$C_6$ alkyl and $C_1$-$C_6$ alkoxy, and each of $R_2$ and $R_5$, which may be identical or different from each other, is independently selected from a group consisting of hydrogen, hydroxy, halogen and trifluoromethyl.

8. The health functional food according to claim 7, wherein the compound of Chemical Formula 1 is a compound of Chemical Formula 7, Chemical Formula 8 or Chemical Formula 9:

[Chemical Formula 7]

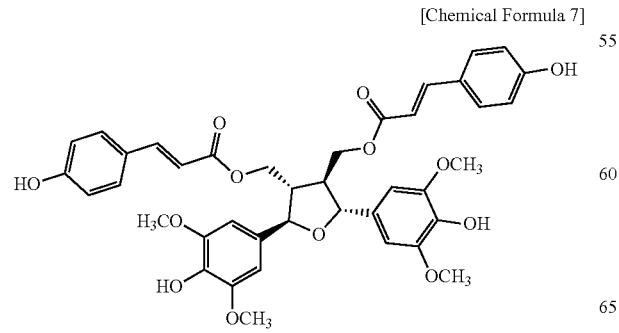

[Chemical Formula 8]

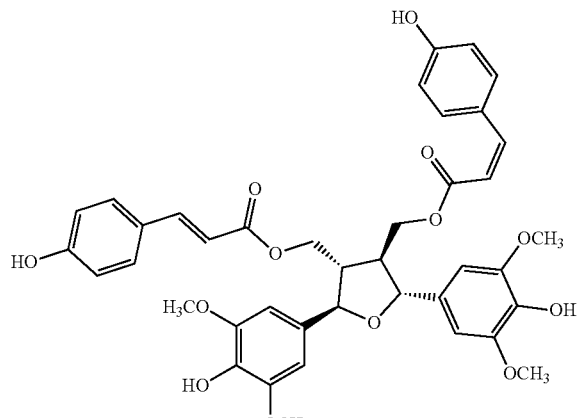

[Chemical Formula 9]

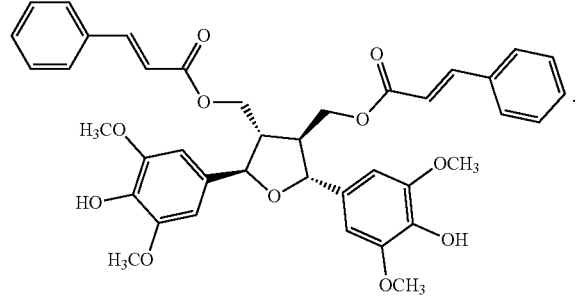

9. The health functional food according to claim 6, which promotes osteoblast differentiation and inhibits adipocyte differentiation.

10. The health functional food according to claim 9, which treats obesity and metabolic bone disease.

11. A compound of Chemical Formula 1:

[Chemical Formula 1]

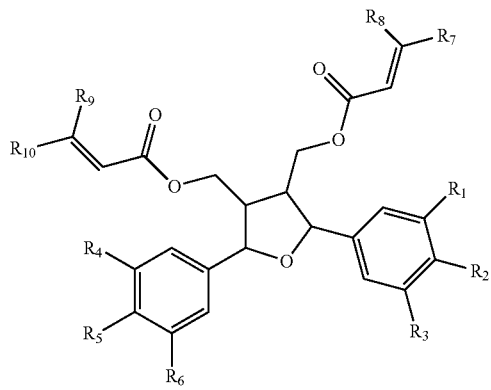

wherein each of $R_1$, $R_2$, $R_3$, $R_4$, $R_5$ and $R_6$, which may be identical or different from each other, is independently selected from a group consisting of hydrogen, hydroxy, $C_1$-$C_6$ alkyl, $C_1$-$C_6$ alkoxy, halogen and trifluoromethyl, and wherein each of $R_7$, $R_8$, $R_9$ and $R_{10}$, which may be identical or different from each other, is independently hydrogen or phenyl, with the proviso that $R_8$ and $R_{10}$ are phenyl if $R_7$ and $R_9$ are hydrogen and $R_8$ and $R_{10}$ are hydrogen if $R_7$ and $R_9$ are phenyl and the phenyl is unsubstituted or substituted with a substituent selected from a group consisting of hydroxy, halogen and trifluoromethyl.

12. The compound according to claim 11, wherein each of $R_1$, $R_3$, $R_4$ and $R_6$, which may be identical or different from each other, is independently selected from a group consisting of $C_1$-$C_6$ alkyl and $C_1$-$C_6$ alkoxy, and each of $R_2$ and $R_5$, which may be identical or different from each other, is independently selected from a group consisting of hydrogen, hydroxy, halogen and trifluoromethyl.

13. The compound according to claim 12, wherein the compound of Chemical Formula 1 is a compound of Chemical Formula 7, Chemical Formula 8 or Chemical Formula 9:

[Chemical Formula 7]

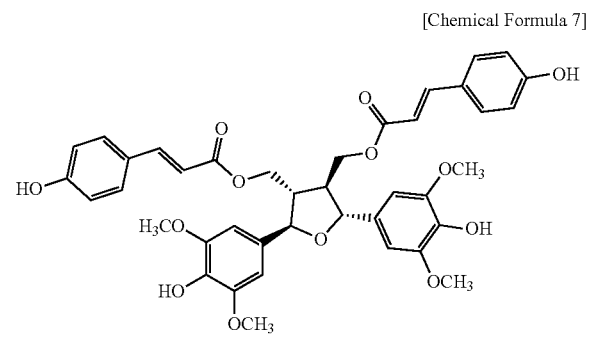

[Chemical Formula 8]

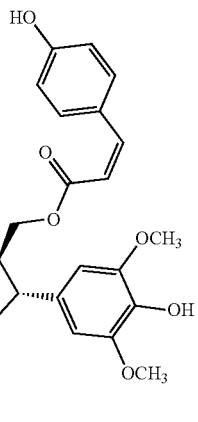

[Chemical Formula 9]

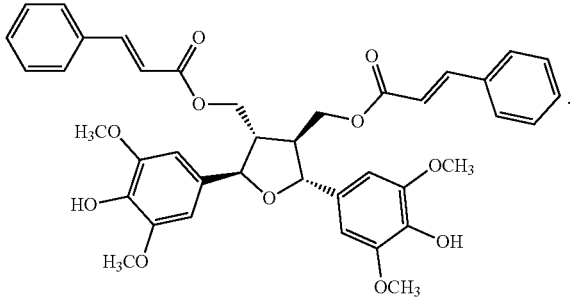

14. A method for preparing a compound of Chemical Formula 7, comprising: a step of preparing a compound of Chemical Formula 6 by reacting a compound of Chemical Formula 4 with a compound of Chemical Formula 5; and a step of removing the methoxymethyl (MOM) protecting group from the compound of Chemical Formula 6:

[Chemical Formula 4]

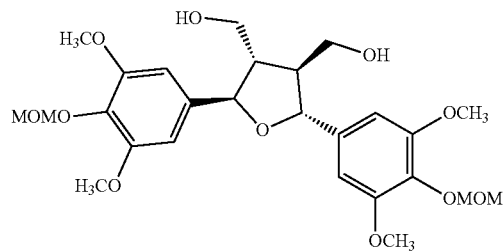

[Chemical Formula 5]

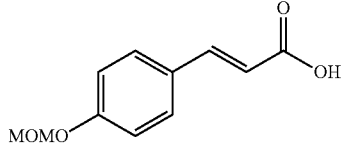

[Chemical Formula 6]

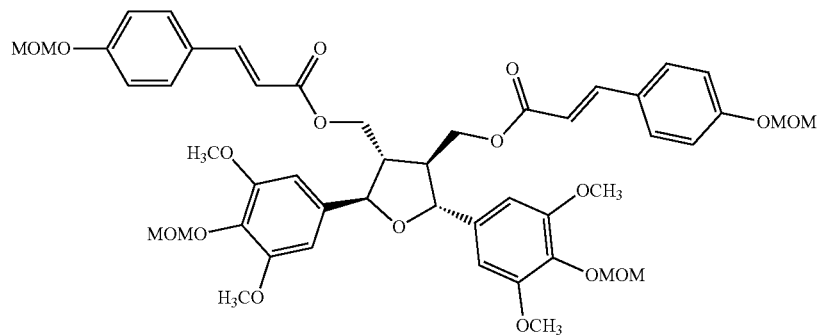

-continued

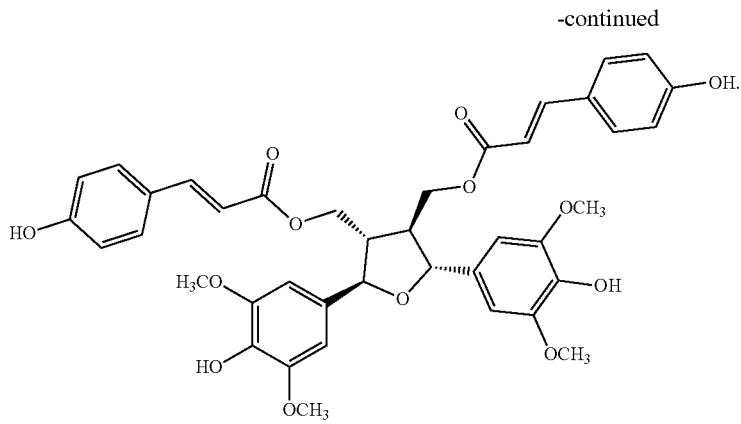

15. The method for preparing a compound of Chemical Formula 7 according to claim 14, further comprising:
    preparing a compound of Chemical Formula 3 by reacting a compound of Chemical Formula 2 with chloromethyl methyl ether; and
    preparing the compound of Chemical Formula 4 by reacting the compound of Chemical Formula 3 with diisobutylaluminum hydride:

[Chemical Formula 2]

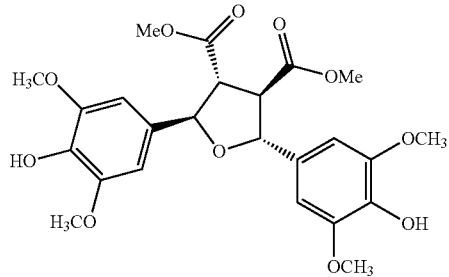

-continued

[Chemical Formula 3]

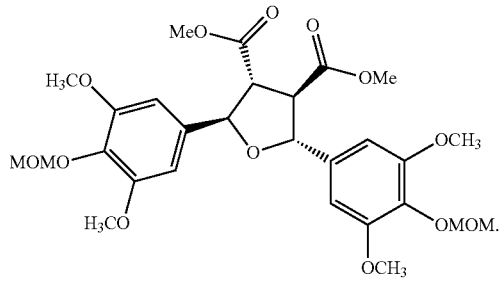

16. The method for preparing a compound of Chemical Formula 7 according to claim 15, wherein the compound of Chemical Formula 2 is synthesized from 4-hydroxy-3,5-dimethoxycinnamic acid.

17. The compound of claim 11, having the activity of promoting osteoblast differentiation and inhibiting adipocyte differentiation.

* * * * *